US008034936B2

(12) United States Patent (10) Patent No.: US 8,034,936 B2
Friderichs et al. (45) Date of Patent: *Oct. 11, 2011

(54) SPIROCYCLIC CYCLOHEXANE COMPOUNDS USEFUL TO TREAT SUBSTANCE DEPENDENCY

(75) Inventors: Elmar Friderichs, Stolberg (DE); Babette-Yvonne Koegel, Langerwehe (DE); Klaus Linz, Bonn (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,274

(22) Filed: Nov. 4, 2010

(65) Prior Publication Data

US 2011/0053970 A1 Mar. 3, 2011

Related U.S. Application Data

(60) Division of application No. 11/870,051, filed on Oct. 10, 2007, which is a continuation of application No. PCT/EP2006/003176, filed on Apr. 7, 2006.

(30) Foreign Application Priority Data

Apr. 11, 2005 (DE) .................. 10 2005 016 460

(51) Int. Cl.
*A61K 31/4353* (2006.01)
*C07D 401/04* (2006.01)
(52) U.S. Cl. ........................ 546/18; 514/278
(58) Field of Classification Search .............. 546/18; 514/278
See application file for complete search history.

(56) References Cited

U.S. PATENT DOCUMENTS

| 7,332,519 B2 | 2/2008 | Hinze et al. |
| 7,485,634 B2 | 2/2009 | Martin et al. |
| 7,547,707 B2 | 6/2009 | Hinze et al. |
| 7,595,311 B2 | 9/2009 | Busch et al. |
| 2005/0192333 A1 | 9/2005 | Hinze et al. |
| 2006/0004034 A1 | 1/2006 | Hinze et al. |
| 2006/0235012 A1 | 10/2006 | Davidson et al. |
| 2007/0149557 A1 | 6/2007 | Collins et al. |
| 2008/0280942 A1 | 11/2008 | Diaz-Fernandez et al. |
| 2009/0042866 A1 | 2/2009 | Lennox et al. |
| 2009/0326218 A1 | 12/2009 | Martin et al. |

FOREIGN PATENT DOCUMENTS

| WO | WO 03/039469 A2 | 5/2003 |
| WO | WO 2004/043967 A1 | 5/2004 |
| WO | WO 2005/066183 A1 | 7/2005 |

OTHER PUBLICATIONS

Zaratin, P.F., et al. "Modification of Nociception and Morphine Tolerance by the Selective Opiate Receptor-Like Orphan Receptor Antagonist (−)-cis-1-Methyl-7-[[4-(2,6-dichlorophenyl)piperidin-1-yl]methyl]-6,7,8,9-tetrahydro-5H-benzocyclohepten-5-ol (SB-612111)", vol. 308, No. 2 (2004) pp. 454-461.

Nurulain Zaveri, "Peptide and nonpeptide ligands for the nociceptin/orphanin FQ receptor ORL1: Research tools and potential therapeutic agents", XP-002393013, Life Sciences 73 (2003) pp. 663-678.
Calo, Girolamo et al., "Pharmacology of nociceptin and its receptor: a novel therapeutic target", XP-002303597, British Journal of Pharmacology (2000) vol. 129, pp. 1261-1283.
Kotlinska, Jolanta et al., "Orphanin FQ/Nociceptin Inhibits Morphine Withdrawal", XP-002393014, Life Sciences, (2000) vol. 66, No. 8, pp. 119-123.
Giannuario, Amalia DI., et al. "Orphanin FQ reduces morphine-induced dopamine release in the nucleus accumbens: a microdialysis study in rats", XP-002393015, Neuroscience Letters 272 (1999) pp. 183-186.
Murphy, Niall P., et al. "Orphanin FQ/nociceptin blocks acquisition of morphine place preference" XP-002393016, Brain Research 832 (1999) pp. 168-170.
Bignan, Gilles C., et al. "Recent advances towards the discovery of ORL-1 receptor agonists and antagonists" XP-002393017, Expert Opinion Ther. Patents (2005) pp. 257-388.
Shoblock James R., et al. "The effect of a systemically active ORL-1 agonist, Ro 64/6198, on the acquisition, expression, extinction, and reinstatement of morphine conditioned place preference", XP-002393018, Neuropharmacology 29 (2005) pp. 439-446.
International Search Report dated Aug. 31, 2006 (Four (4) pages).
German Search Report dated Oct. 4, 2005 with an English translation of the pertinent portions (Nine (9) pages).
Ali Ardati et al., "Interaction of [$^3$H] Orphanin FQ and $^{125}$I-Tyr14-Orphanin FQ with the Orphanin FQ Receptor: Kinetics and Modulation by Cations and Guanine Nucleotides", The American Society for Pharmacology and Experimental Therapeutics, Molecular Pharmacology, 51:816-824 (1997).
Ulrike Bischoff et al., "Effects of fluoroquinolones on HERG currents", European Journal of Pharmacology 406 (2000) 341-343, www.elsevier.nl/locate/ejphar.
Bernard A. Schwetz, DVM, Phd., "Labeling Changes for Orlaam", JAMA, Jun. 6, 2001—vol. 285, No. 21, www.jama.com.
Jiesheng Kang et al., "Interactions of the narcotic l-α-acetylmethadol with human cardiac K$^+$ channels", European Journal of Pharmacology 458 (2003) 25-29, Elsevier.
Alexander N. Katchman et al., "Influence of Opioid Agonists on Cardiac Human Ether-a-go-go related Gene K$^+$ Currents", The Journal of Pharmacology and Experimental Therapeutics, vol. 303, No. 2, 688-694, 2002, The American Society for Pharmacology and Experimental Therapeutics.
Craig A. Kornick et al., "QTc interval prolongation associated with intravenous methadone", Pain 105 (2003) 499-506.
J. K. Saelens et al., "The Mouse Jumping Test—A Simple Screening Method to Estimate the Physical Dependence Capacity of Analgesics", Arch. Int. Pharmacodyn. 190, 213-218 (1971).
James R. Weeks et al., "The Cardiovascular Pharmacology of Prostacyclin (PGI$_2$) in the Rat", Prostaglandins, Apr. 1979, vol. 17, No. 4, pp. 501-513.

*Primary Examiner* — Rita Desai
(74) *Attorney, Agent, or Firm* — Crowell & Moring LLP

(57) ABSTRACT

Spirocyclic cyclohexane compounds useful in pharmaceutical compositions for use in the treatment of substance dependency.

19 Claims, 3 Drawing Sheets

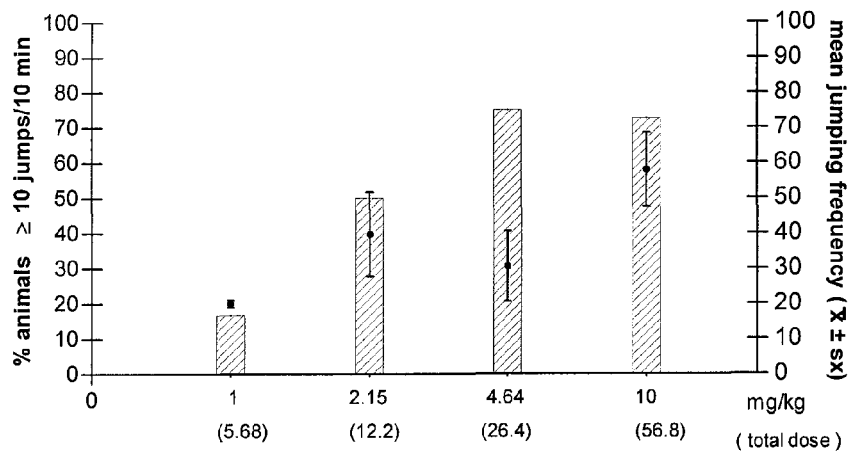
Fig. 1: Withdrawal symptom jumps after levomethadone
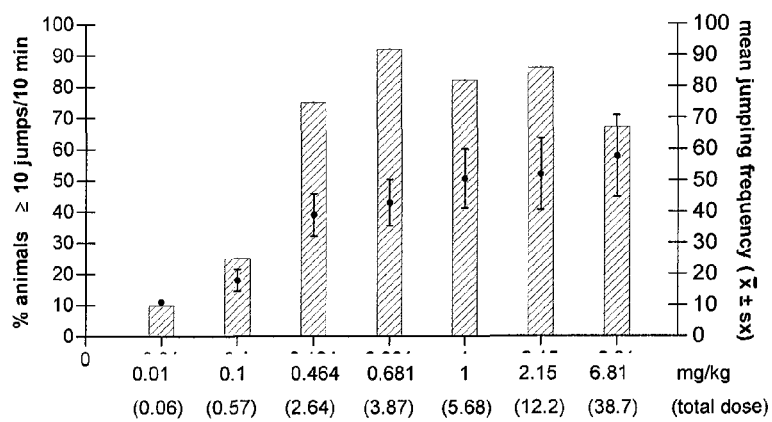
Fig. 2: Withdrawal symptom jumps after compound m

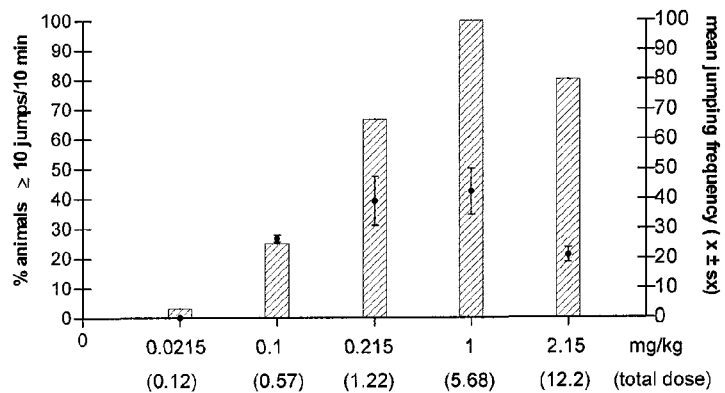
Fig. 3: Withdrawal symptom jumps after compound n
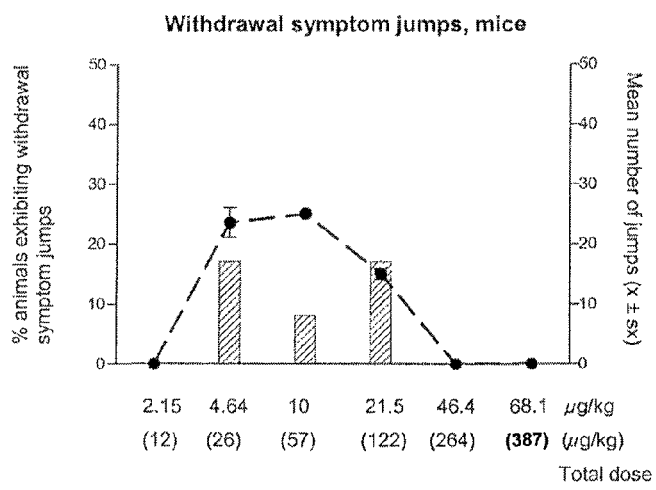
Fig. 4: Withdrawal symptom jumps according to Example 1

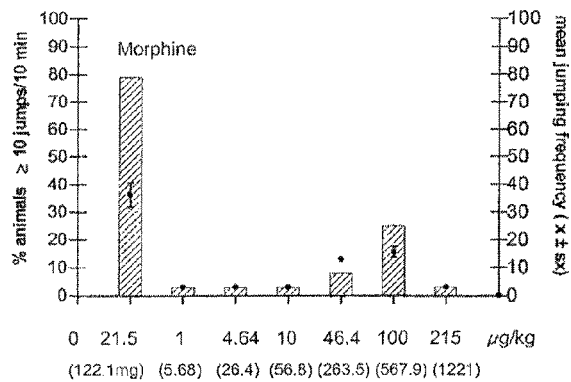
Fig. 5: Withdrawal symptom jumps according to Example 3; left column: morphine (21.5 mg/kg) as comparison substance
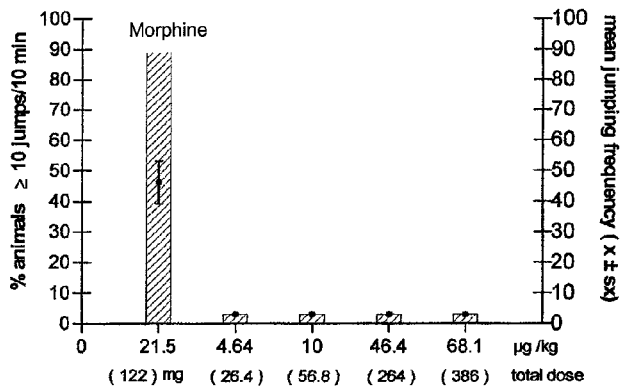
Fig. 6: Withdrawal symptom jumps according to Example 4; left column: morphine (21,5 mg/kg) as comparison substance

SPIROCYCLIC CYCLOHEXANE COMPOUNDS USEFUL TO TREAT SUBSTANCE DEPENDENCY

CROSS REFERENCE TO RELATED APPLICATIONS

This application is a division of co-pending application Ser. No. 11/870,051, filed Oct. 10, 2007, which in turn was a continuation of international patent application No. PCT/EP2006/003176, filed Apr. 7, 2006, designating the United States of America, and published in German on Oct. 19, 2006 as WO 2006/108565, the entire disclosure of which is incorporated herein by reference. Priority is claimed based on Federal Republic of Germany patent application No. DE 10 2005 016 460.9, filed Apr. 11, 2005.

BACKGROUND OF THE INVENTION

Opiate dependency is a major medical and social problem, which requires intensive medical care. A standard treatment is opiate substitution by a specially suitable μ-opioid. Clinically established substances for the substitution therapy of opiate dependency are:
- methadone (racemate, in rare cases levomethadone)
- LAAM (α-acetylmethadol)
- buprenorphine All three substances are used to achieve the same objectives:
- satisfaction of the opiate craving but without any "kick" and with a significantly reduced euphoria
- avoidance of bodily withdrawal symptoms
- re-socialisation of the patient (controlled rehabilitation, ability to work, withdrawal from the drug-related environment)
- long-term reduction in the opiate dosage until complete abstinence is achieved.

In order that these effects can be achieved, the substitution therapeutic agents must have the following properties:
- oral (possibly also cutaneous) effect availability
- long effective duration (1-3 days, possibly even longer)
- high potency
- low euphorisation
- low "kick"
- low withdrawal symptoms
- good long-term compatibility (only slight constipation, good cardiovascular compatibility)

The standard therapeutic agents used up to now exhibit only some of these properties, with the result that their therapeutic use is to some extent unsatisfactory. The basic problems with the current standard therapeutic agents are the following: methadone has a high potential for misuse. On account of the only moderate action duration a daily administration is necessary. In addition constipation is a side effect. LAAM has the disadvantage of a high cardiotoxicity and can trigger Torsade de Pointes arrhythmia. Buprenorphine has a high toxicity when combined with benzodiazepines.

US 2006/004034 A1 (=WO 04/43967) and US 2005/192333 A1 (=WO 2005/066183) describe compounds that are particularly suitable for the treatment of pain, but also inter alia for the treatment of withdrawal symptoms as well as for reducing the potential for opioid addiction. It has now been found that that selected compounds from these patent applications are particularly suitable for use as substitution therapeutic agents in treatment of substance dependence.

SUMMARY OF THE INVENTION

The object of the present invention was to provide a new method of treating substance dependence with substitution therapeutic agents.

Another object of the invention is to provide a method of treating opioid dependency which has advantages compared to the standard therapies.

These and other objects have been achieved in accordance with the present invention by providing spirocyclic cyclohexane compounds corresponding to formula I

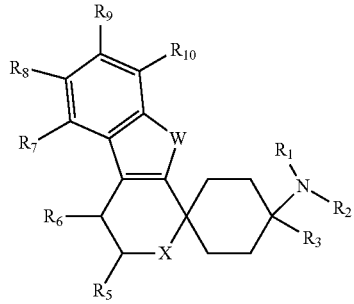

wherein
$R^1$ and $R^2$ independently of one another denote H or $CH_3$ or together denote $(CH_2)_4$ or $(CH_2)_5$ and form a ring with the nitrogen to which they are bound, wherein $R^1$ and $R^2$ do not simultaneously denote H;
$R^3$ denotes phenyl, benzyl or heteroaryl in each case unsubstituted or singly or multiply substituted with F, Cl, OH, CN or $OCH_3$;
W denotes $NR^4$, O or S, where
  $R^4$ denotes H; $C_{1-5}$-alkyl, phenyl; phenyl, $COR^{12}$ bound via a $C_{1-3}$ alkyl group; $SO_2R^{12}$, where
    $R^{12}$ denotes H; $C_{1-7}$-alkyl, branched or unbranched, saturated or unsaturated, unsubstituted or singly or multiply substituted with OH, F or $COOC_{1-4}$-alkyl; $C_{4-6}$-cycloalkyl; aryl or heteroaryl, unsubstituted or singly or multiply substituted with F, Cl, Br, $CF_3$, $OCH_3$, $C_{1-4}$-alkyl, branched or unbranched, substituted; or phenyl or heteroaryl bound via saturated or unsaturated $C_{1-3}$ alkyl, unsubstituted or singly or multiply substituted with F, Cl, Br, $CF_3$, $OCH_3$, $C_{1-4}$-alkyl, branched or unbranched, substituted; or $C_{5-6}$-cycloalkyl bound via saturated or unsaturated $C_{1-3}$-alkyl; $OR^{13}$; $NR^{14}R^{15}$;
$R^5$ denotes H; $COOR^{13}$, $CONR^{13}$, $OR^{13}$; $C_{1-5}$-alkyl, saturated or unsaturated, branched or unbranched, unsubstituted or singly or multiply substituted with OH, F, $CF_3$ or CN;
$R^6$ denotes H; or
$R^5$ and $R^6$ together denote $(CH_2)_n$ where n=2, 3, 4, 5 or 6, wherein individual hydrogen atoms may also be replaced by F, Cl, $NO_2$, $CF_3$, $OR^{13}$, CN or $C_{1-5}$-alkyl;
$R^7$, $R^8$, $R^9$ and $R^{10}$ independently of one another denote H, F, Cl, Br, $NO_2$, $CF_3$, OH, $OCH_3$, CN, $COOR^{13}$, $NR^{14}R^{15}$; $C_{1-5}$-alkyl, heteroaryl, unsubstituted or singly or multiply substituted with benzyl, $CH_3$, Cl, F, $OCH_3$ or OH; where
  $R^{13}$ denotes H or $C_{1-5}$-alkyl; and
  $R^{14}$ and $R^{15}$ independently of one another denote H or $C_{1-5}$-alkyl;
X denotes O, S, SO, $SO_2$ or $NR^{17}$; where
  $R^{17}$ denotes H; $C_{1-5}$-alkyl, saturated or unsaturated, branched or unbranched; $COR^{12}$ or $SO_2R^{12}$,
in the form of their pure diastereomers, their racemates, their pure enantiomers, or in the form of mixtures of the stereoisomers in an arbitrary mixture ratio; as bases or in the form of their salts, in particular of the physiologically compatible salts or salts of physiological compatible acids or cations; or in the form of their solvates, wherein the ratio of the ORL1 receptor affinity to the μ-opioid receptor affinity is 0.3 or greater, for the treatment of substance dependency.

As used herein, the term salt is understood to denote any form of the active constituent according to the invention in which this adopts an ionic form or is charged, and is coupled to a counter-ion (a cation or anion) and/or is present in solution. The term is also understood to include complexes of the active constituent with other molecules and ions, in particular complexes which are complexed via ionic interactions. In particular the term is understood to include (and this is also a preferred embodiment of the present invention) physiologically compatible salts, in particular physiologically compatible salts with cations or bases and physiologically compatible salts with anions or acids or also a salt formed with a physiologically compatible acid or with a physiologically compatible cation.

The term salt formed with a physiologically compatible acid is understood within the context of the present invention to denote salts of the respective active constituent with inorganic or organic acids, which are physiologically compatible—especially when used in humans and/or mammals. The hydrochloride and citrate are particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutanic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid and/or aspartic acid.

In the context of the present invention, the expressions "$C_{1-3}$-alkyl" "$C_{1-5}$-alkyl", "$C_{1-7}$-alkyl" and "$C_{1-4}$-alkyl" include acyclic saturated or unsaturated hydrocarbon radicals, which may be branched or straight-chain, with respectively 1, 2 or 3 C atoms, 1, 2, 3, 4 or 5 C atoms, 1, 2, 3, 4, 5, 6 or 7 C atoms or 1, 2, 3 or 4 C atoms. Unsaturated compounds have at least one C—C double bond or at least one C—C triple bond. From the above group alkyl is advantageously selected, which includes methyl, ethyl, n-propyl, 2-propyl, n-butyl, iso-butyl, sec.-butyl, tert.-butyl, n-pentyl, iso-pentyl, neopentyl, n-hexyl, 2-hexyl; ethylenyl (vinyl), ethinyl, propenyl (—CH$_2$CH=CH$_2$, —CH=CH—CH$_3$, —C(=CH$_2$)—CH$_3$), propinyl (—CH—C≡CH, —C≡C—CH$_3$), 1,1-dimethylethyl, 1,1-dimethylpropyl, butenyl, butinyl, pentenyl and pentinyl.

For the purposes of the present invention, the expression "$C_{5-6}$-cycloalkyl" denotes cyclic hydrocarbons with 5 or 6 Carbon atoms, wherein the hydrocarbons may be saturated or unsaturated (but not aromatic). From the above group $C_{5-6}$-cycloalkyl is advantageously selected, which includes cyclopentyl and cyclohexyl.

The expression "heteroaryl" denotes a 5-, 6- or 7-membered cyclic aromatic radical, which contains at least 1, but possibly also 2, 3, 4 or 5 heteroatoms, wherein the heteroatoms are identical or different and the heterocycle may be unsubstituted or singly or multiply substituted; in the case of substitution in the heterocycle, the substituents may be identical or different and in any arbitrary and possible position of the heteroaryl. Preferred heteroatoms are nitrogen, oxygen and sulfur. It is preferred to select the heteroaryl radical from the group comprising pyrrolyl, furyl (furanyl), benzofuranyl, thienyl, pyrazolyl, imidazolyl, thiazolyl, oxazolyl, isoxazolyl, pyridinyl, or carbazolyl, wherein the bonding to the compounds of the general structure I can be effected by any arbitrary and possible ring member of the heteroaryl radical. Pyridyl and thienyl are particularly preferred. Pyrazolyl and furyl are also particularly preferred.

Animal experiment investigations with substances from US 2006/004034 A1 and US 2005/192333 A1 have surprisingly shown that the substances with a particularly high ORL1 affinity, which is not more than one order of magnitude less than the μ-opioid receptor affinity, are particularly suitable for an opiate substitution and thus have the potential for a significant improvement in the substitution therapy.

Among the spiro compounds described in US 2006/004034 A1 and US 2005/066183 A1 are compounds with higher and lower ORL1 components. In naloxone-induced withdrawal symptoms in mice it was shown that spirocyclic compounds with an ORL1 component which is not weaker by a factor of more than 10 than the μ-component, can suppress withdrawal symptoms. Compounds with a weaker ORL1 component on the other hand trigger withdrawal symptoms. In the "withdrawal jumping" test mice are repeatedly treated over a defined period with the test substance. In the case of a μ-opioid a systemic dependency is induced within this period. At the end of the treatment the effect of the opioid is cancelled immediately by administering naloxone, a μ-antagonist. When the mice become systemically dependent they exhibit characteristic withdrawal symptoms, which are manifested in the form of jumping movements (Saelens J K, Arch Int Pharmacodyn 190: 213-218, 1971).

The compounds according to the invention have on account of the ORL1 active component additional properties which the standard substances such as methadone, LAAM or buprenorphine do not possess and which improve the treatment. In withdrawal jumping in mice it was shown that in the case of mice that had been treated with combined μ-/ORL1 agonists, as in Example 1, Example 3 or Example 4, no, or only a minimal, withdrawal behaviour is triggered by naloxone. This confirms that the withdrawal symptoms are suppressed by the ORL1 component. This results in a significant advantage if these substances are used in the treatment of withdrawal symptoms, since the occurrence of withdrawal symptoms is one of the most important side effects of this treatment and often leads to non-compliance. The ORL1/μ-affinity should be 0.3 or greater. It is preferred if the ORL1/μ-affinity ratio is ≧1, particularly preferably ≧1.7.

The result that the compounds according to the invention with a stronger ORL1 component suppress the withdrawal jumping that should be triggered by the μ-component, demonstrates the efficacy of these compounds for use in substitution therapy. It is therefore preferred if the substance dependency is opiate dependency, for example dependency on alfentanil, buprenorphine, butorphanol, codeine, dextromoramide, dextropropoxyphene, dezocin, dihydrocodeine, diphenoxylate, ethylmorphine, hydrocodone, hydromorphone, ketobemidone, LAAM, levorphanol, meptazinol, oxycodon, oxymorphone, fentanyl, morphine, heroin, pethidine, sufentanil or tilidin, preferably morphine, methadone or heroin.

The spirocyclic cyclohexane derivatives according to the invention can also be used in combination with an opioid receptor antagonist, preferably with naloxone.

In the synthesis of the compounds according to the invention, as described in US 2006/004034 A1 and US 2005/066183 A1, two or more diastereomers can occur. In most cases the non-polar diastereomers have compared to the polar diastereomers a higher affinity for the two investigated opiate receptors. It is therefore preferred if the substances according to the invention are present in the form of the non-polar diastereomer.

Spirocyclic cyclohexane derivatives in which $R^3$ denotes heteroaryl are preferred in the context of the present invention. Also preferred in the context of the present invention are spirocyclic cyclohexane derivatives in which $R^3$ denotes phenyl, unsubstituted or singly or multiply substituted with F, OH, Cl or $OCH_3$, or denotes benzyl.

Also preferred are spirocyclic cyclohexane derivatives in which $R^1$ and $R^2$ denote $CH_3$ or H, in which case $R^1$ and $R^2$ do not simultaneously denote H.

It is preferred to use spirocyclic cyclohexane derivatives selected from the group:
1  1,1-(3-dimethylamino-3-phenylpentamethylene)-1,3,4,9-tetrahydropyrano[3,4-b)]indole;
2  1,1-(3-dimethylamino-3-benzylpentamethylene)-2-(2-nitrobenzoyl)-1,3,4,9-tetrahydro-2,9-diazafluorene;
3  1,1-(3-dimethylamino-3-phenylpentamethylene)-6-fluoro-1,3,4,9-tetrahydropyrano[3,4-b]indole;
4  1,1-(3-dimethylamino-3-(2-thienyl)pentamethylene)-1,3,4,9-tetrahydropyrano[3,4-b]indole;
5  1,1-(3-dimethylamino-3-phenylpentamethylene)-3-methyl-1,3,4,9-tetrahydropyrano[3,4-b)]indole;
6  1,1-(3-dimethylamino-3-phenylpentamethylene)-3,6-dimethyl-1,3,4,9-tetrahydropyrano[3,4-b)]indole;
7  1,1-(3-dimethylamino-3-(4-fluorophenyl)pentamethylene)-1,3,4,9-tetrahydro-pyrano[3,4-b]indole;
8  1,1-(3-dimethylamino-3-phenylpentamethylene)-3-hydroxymethyl-1,3,4,9-tetrahydro-2,9-diazafluorene;
9  1,1-(3-dimethylamino-3-phenylpentamethylene)-2-(2,3,4,5,6-pentafluoro-benzoyl)-1,3,4,9-tetrahydro-2,9-diazafluorene;
10  1,1-(3-dimethylamino-3-phenylpentamethylene)-2-(methoxycarbonyl)-1,3,4,9-tetrahydro-2,9-diazafluorene;
11  1,1-(3-dimethylamino-3-phenylpentamethylene)-7-fluoro-1,3,4,9-tetrahydro-2,9-diazafluorene;
12  1,1-(3-dimethylamino-3-phenylpentamethylene)-1,3,4,9-tetrahydro-2-aza-9-oxafluorene;
13  1,1-(3-dimethylamino-3-(3-fluorophenyl)pentamethylene)-1,3,4,9-tetrahydro-2,9-diazafluorene;
14  1,1-(3-dimethylamino-3-phenylpentamethylene)-2-acetyl-1,3,4,9-tetrahydro-2,9-diazafluorene;
15  1,1-(3-dimethylamino-3-(3-fluorophenyl)pentamethylene)-1,3,4,9-tetrahydropyrano[3,4-b)]indole;
16  1,1-(3-dimethylamino-3-phenylpentamethylene)-6-chloro-3-methyl-1,3,4,9-tetrahydropyrano[3,4-b]indole;
17  1,1-(3-dimethylamino-3-(2-pyridyl)pentamethylene)-1,3,4,9-tetrahydro-2,9-diazafluorene;
18  1,1-(3-dimethylamino-3-(3-thienyl)pentamethylene)-6-fluoro-1,3,4,9-tetrahydropyrano[3,4-b]indole;
19  1,1-(3-dimethylamino-3-phenylpentamethylene)-2-acetyl-7-fluoro-1,3,4,9-tetrahydro-2,9-diazafluorene;
20  1,1-(3-dimethylamino-3-phenylpentamethylene)-1,3,4,9-tetrahydro-2,9-diazafluorene;
21  1,1-(3-dimethylamino-3-phenylpentamethylene)-3-methyl-1,3,4,9-tetra-hydropyrano[3,4-b]indole;
22  1,1-(3-dimethylamino-3-phenylpentamethylene)-1,3,4,9-tetrahydro-2-thia-9-azafluorene;
23  1,1-(3-dimethylamino-3-phenylpentamethylene)-3-methyl-6-nitro-1,3,4,9-tetrahydropyrano[3,4-b]indole;
24  1,1-(3-dimethylamino-3-(3-thienyl)pentamethylene)-1,3,4,9-tetrahydro-pyrano[3,4-b]indole;
25  1,1-(3-dimethylamino-3-(4-fluorophenyl)pentamethylene)-1,3,4,9-tetrahydro-2,9-diazafluorene;
26  1,1-(3-dimethylamino-3-phenylpentamethylene)-3-methyl-1,3,4,9-tetrahydro-2,9-diazafluorene;
27  1,1-(3-dimethylamino-3-phenylpentamethylene)-2-oxo-1,3,4,9-tetrahydro-2-thia-9-azafluorene;
28  1,1-(3-dimethylamino-3-phenylpentamethylene)-1,3,4,9-tetrahydro-2-thia-9-azafluorene;
29  1,1-(3-dimethylamino-3-(2-thienyl)pentamethylene)-6-fluoro-1,3,4,9-tetrahydro-pyrano[3,4-b]indole;
30  1,1-(3-dimethylamino-3-phenylpentamethylene)-3-methyl-1,3,4,9-tetrahydro-2,9-diazafluorene;
31  1,1-(3-dimethylamino-3-phenylpentamethylene)-6-fluoro-3-methyl-1,3,4,9-tetrahydropyrano[3,4-b]indole;
32  1,1-(3-dimethylamino-3-phenylpentamethylene)-6-hydroxy-1,3,4,9-tetrahydropyrano[3,4-b]indole;
33  1,1-(3-dimethylamino-3-(3-hydroxyphenyl)pentamethylene)-1,3,4,9-tetrahydropyrano[3,4-b]indole;
34  1,1-(3-dimethylamino-3-phenylpentamethylene)-1,3,4,9-tetrahydro-2-thia-9-azafluorene;
35  6,6-(3-dimethylamino-3-phenylpentamethylene)-1,2,3,4,4a,6,7,11c-octahydro-5-oxa-7-aza-benzo[c]fluorine;
36  1,1-(3-dimethylamino-3-phenylpentamethylene)-6-methyl-1,3,4,9-tetrahydropyrano[3,4-b]indole;
37  1,1-(3-dimethylamino-3-(4-fluorophenyl)pentamethylene)-2-acetyl-1,3,4,9-tetrahydro-2,9-diazafluorene;
38  1,1-(3-dimethylamino-3-benzylpentamethylene)-1,3,4,9-tetrahydro-2,9-diazafluorene;
39  1,1-(3-dimethylamino-3-phenylpentamethylene)-6-fluoro-1,3,4,9-tetrahydro-2,9-diazafluorene;
40  1,1-(3-dimethylamino-3-phenylpentamethylene)-6-methyl-1,3,4,9-tetrahydro-2,9-diazafluorene;
41  1,1-(3-dimethylamino-3-phenylpentamethylene)-6-bromo-3-methyl-1,3,4,9-tetrahydropyrano[3,4-b]indole;
42  1,1-(3-dimethylamino-3-phenylpentamethylene)-6-fluoro-1,3,4,9-tetrahydropyrano[3,4-b]indole;
43  1,1-(3-dimethylamino-3-phenylpentamethylene)-6-bromo-1,3,4,9-tetrahydropyrano[3,4-b]indole;
44  1,1-(3-dimethylamino-3-phenylpentamethylene)-6-methoxy-1,3,4,9-tetra-hydropyrano[3,4-b]indole;
45  1,1-(3-(1-Pyrrolidyl)-3-phenylpentamethylene)-1,3,4,9-tetrahydropyrano[3,4-b]indole;
46  1,1-(3-dimethylamino-3-phenylpentamethylene)-7,8-dichloro-1,3,4,9-tetrahydropyrano[3,4-b]indole;
47  1,1-(3-dimethylamino-3-phenylpentamethylene)-6-(1-benzyl-pyrazol-4-yl)-1,3,4,9-tetrahydro-pyrano[3,4-b]indole;
48  1,1-(3-Methylamino-3-(2-thienyl)pentamethylene)-1,3,4,9-tetrahydro-pyrano[3,4-b]indole;
49  1,1-(3-methylamino-3-(2-thienyl)pentamethylene)-6-fluoro-1,3,4,9-tetrahydro-pyrano[3,4-b]indole;
50  1,1-(3-dimethylamino-3-(3-fluorophenyl)pentamethylene)-2-cinnamoyl-1,3,4,9-tetrahydro-2,9-diazafluorene;
51  1,1-(3-dimethylamino-3-(3-fluorophenyl)pentamethylene)-2-(3,3-dimethylbutanoyl)-1,3,4,9-tetrahydro-2,9-diazafluorene;
52  1,1-(3-dimethylamino-3-(3-fluorophenyl)pentamethylene)-2-(cyclopentylcarbonyl)-1,3,4,9-tetrahydro-2,9-diazafluorene;
53  1,1-(3-dimethylamino-3-phenylpentamethylene)-2-(3,3-dimethylbutanoyl)-1,3,4,9-tetrahydro-2,9-diazafluorene;
54  1,1-(3-dimethylamino-3-(3-fluorophenyl)pentamethylene)-2-(pentanoyl)-1,3,4,9-tetrahydro-2,9-diazafluorene;
55  1,1-(3-dimethylamino-3-(3-fluorophenyl)pentamethylene)-2-(2-furylcarbonyl)-1,3,4,9-tetrahydro-2,9-diazafluorene;
56  1,1-(3-dimethylamino-3-phenylpentamethylene)-2-(2-furylcarbonyl)-1,3,4,9-tetrahydro-2,9-diazafluorene;
57  1,1-(3-dimethylamino-3-(3-fluorophenyl)pentamethylene)-2-(4-fluorobenzoyl)-1,3,4,9-tetrahydro-2,9-diazafluorene;

58 1,1-(3-dimethylamino-3-(3-fluorophenyl)pentamethylene)-2-(2-methoxybenzoyl)-1,3,4,9-tetrahydro-2,9-diazafluorene;

59 1,1-(3-dimethylamino-3-phenylpentamethylene)-2-(3-methylbutanoyl)-1,3,4,9-tetrahydro-2,9-diazafluorene;

60 1,1-(3-dimethylamino-3-(3-fluorophenyl)pentamethylene)-2-(cyclohexylcarbonyl)-1,3,4,9-tetrahydro-2,9-diazafluorene;

61 1,1-(3-dimethylamino-3-(3-fluorophenyl)pentamethylene)-2-benzoyl-1,3,4,9-tetrahydro-2,9-diazafluorene;

62 1,1-(3-dimethylamino-3-phenylpentamethylene)-2-(cyclohexylcarbonyl)-1,3,4,9-tetrahydro-2,9-diazafluorene;

63 1,1-(3-dimethylamino-3-(3-fluorophenyl)pentamethylene)-2-(phenylacetyl)-1,3,4,9-tetrahydro-2,9-diazafluorene;

64 1,1-(3-dimethylamino-3-(3-fluorophenyl)pentamethylene)-2-(4-methoxybenzoyl)-1,3,4,9-tetrahydro-2,9-diazafluorene;

65 1,1-(3-dimethylamino-3-phenylpentamethylene)-2-(4-trifluoromethylbenzoyl)-1,3,4,9-tetrahydro-2,9-diazafluorene;

66 1,1-(3-dimethylamino-3-(3-fluorophenyl)pentamethylene)-2-(thien-2-ylacetyl)-1,3,4,9-tetrahydro-2,9-diazafluorene;

67 1,1-(3-dimethylamino-3-(3-fluorophenyl)pentamethylene)-2-(phenylacetyl)-1,3,4,9-tetrahydro-2,9-diazafluorene;

68 1,1-(3-dimethylamino-3-(3-fluorophenyl)pentamethylene)-2-butanoyl-1,3,4,9-tetrahydro-2,9-diazafluorene;

69 1,1-(3-dimethylamino-3-benzylpentamethylene)-2-(4-trifluoromethylbenzoyl)-1,3,4,9-tetrahydro-2,9-diazafluorene;

70 1,1-(3-dimethylamino-3-benzylpentamethylene)-2-(3-fluoro-5-trifluoromethylbenzoyl)-1,3,4,9-tetrahydro-2,9-diazafluorene;

71 1,1-(3-dimethylamino-3-(3-fluorophenyl)pentamethylene)-2-(2,3-difluorobenzoyl)-1,3,4,9-tetrahydro-2,9-diazafluorene;

72 1,1-(3-dimethylamino-3-(3-fluorophenyl)pentamethylene)-2-(4-methylbenzoyl)-1,3,4,9-tetrahydro-2,9-diazafluorene;

73 1,1-(3-dimethylamino-3-phenylpentamethylene)-2-(3-phenylpropanoyl)-1,3,4,9-tetrahydro-2,9-diazafluorene;

74 1,1-(3-dimethylamino-3-phenylpentamethylene)-2-(3,4-dichlorobenzoyl)-1,3,4,9-tetrahydro-2,9-diazafluorene;

75 1,1-(3-dimethylamino-3-benzylpentamethylene)-2-cinnamoyl-1,3,4,9-tetrahydro-2,9-diazafluorene;

76 1,1-(3-dimethylamino-3-benzylpentamethylene)-2-(2,6-difluorobenzoyl)-1,3,4,9-tetrahydro-2,9-diazafluorene;

77 1,1-(3-dimethylamino-3-phenylpentamethylene)-2-(3-methoxycarbonylpropanoyl)-1,3,4,9-tetrahydro-2,9-diazafluorene;

78 1,1-(3-dimethylamino-3-(3-fluorophenyl)pentamethylene)-2-(3-chlorobenzoyl)-1,3,4,9-tetrahydro-2,9-diazafluorene;

79 1,1-(3-dimethylamino-3-phenylpentamethylene)-2-(3-fluorobenzoyl)-1,3,4,9-tetrahydro-2,9-diazafluorene;

80 1,1-(3-dimethylamino-3-phenylpentamethylene)-2-(2,6-difluorobenzoyl)-1,3,4,9-tetrahydro-2,9-diazafluorene;

81 1,1-(3-dimethylamino-3-(3-fluorophenyl)pentamethylene)-2-(3,4-dichlorobenzoyl)-1,3,4,9-tetrahydro-2,9-diazafluorene;

82 1,1-(3-dimethylamino-3-benzylpentamethylene)-2-(2,3,4,5,6-pentafluorobenzoyl)-1,3,4,9-tetrahydro-2,9-diazafluorene;

83 1,1-(3-dimethylamino-3-benzylpentamethylene)-2-cyclohexylcarbonyl-1,3,4,9-tetrahydro-2,9-diazafluorene;

84 1,1-(3-dimethylamino-3-phenylpentamethylene)-2-(3-cyclopentylpropanoyl)-1,3,4,9-tetrahydro-2,9-diazafluorene;

85 1,1-(3-dimethylamino-3-(3-fluorophenyl)pentamethylene)-2-(4-fluoro-3-trifluoromethylbenzoyl)-1,3,4,9-tetrahydro-2,9-diazafluorene;

86 1,1-(3-dimethylamino-3-(3-fluorophenyl)pentamethylene)-2-(4-methylbenzoyl)-1,3,4,9-tetrahydro-2,9-diazafluorene;

87 1,1-(3-dimethylamino-3-(3-fluorophenyl)pentamethylene)-2-(3,4,5-trimethoxybenzoyl)-1,3,4,9-tetrahydro-2,9-diazafluorene;

88 1,1-(3-dimethylamino-3-benzylpentamethylene)-2-cyclobutylcarbonyl-1,3,4,9-tetrahydro-2,9-diazafluorene;

89 1,1-(3-dimethylamino-3-benzylpentamethylene)-2-(2,6-dichlorobenzoyl)-1,3,4,9-tetrahydro-2,9-diazafluorene;

90 1,1-(3-dimethylamino-3-(3-fluorophenyl)pentamethylene)-2-(3-methoxybenzoyl)-1,3,4,9-tetrahydro-2,9-diazafluorene;

91 1,1-(3-dimethylamino-3-phenylpentamethylene)-2-(2-thienylcarbonyl)-1,3,4,9-tetrahydro-2,9-diazafluorene;

92 1,1-(3-dimethylamino-3-(3-fluorophenyl)pentamethylene)-2-propanoyl-1,3,4,9-tetrahydro-2,9-diazafluorene;

93 1,1-(3-dimethylamino-3-(3-fluorophenyl)pentamethylene)-2-(2,4-difluorobenzoyl)-1,3,4,9-tetrahydro-2,9-diazafluorene;

94 1,1-(3-dimethylamino-3-(3-fluorophenyl)pentamethylene)-2-(3,5-difluorobenzoyl)-1,3,4,9-tetrahydro-2,9-diazafluorene;

95 1,1-(3-dimethylamino-3-(3-fluorophenyl)pentamethylene)-2-(4-tert.butylbenzoyl)-1,3,4,9-tetrahydro-2,9-diazafluorene;

96 1,1-(3-dimethylamino-3-benzylpentamethylene)-2-(3-methoxycarbonylpropanoyl)-1,3,4,9-tetrahydro-2,9-diazafluorene;

97 1,1-(3-dimethylamino-3-(3-fluorophenyl)pentamethylene)-2-(3,4-difluorobenzoyl)-1,3,4,9-tetrahydro-2,9-diazafluorene;

98 1,1-(3-dimethylamino-3-phenylpentamethylene)-2-(2-ethylhexanoyl)-1,3,4,9-tetrahydro-2,9-diazafluorene;

99 1,1-(3-dimethylamino-3-(3-fluorophenyl)pentamethylene)-2-(2-methylbenzoyl)-1,3,4,9-tetrahydro-2,9-diazafluorene;

100 1,1-(3-dimethylamino-3-phenylpentamethylene)-2-(3-phenylpropanoyl)-1,3,4,9-tetrahydro-2,9-diazafluorene;

101 1,1-(3-dimethylamino-3-(3-fluorophenyl)pentamethylene)-2-(3-fluoro-5-trifluoromethylbenzoyl)-1,3,4,9-tetrahydro-2,9-diazafluorene;

102 1,1-(3-dimethylamino-3-phenylpentamethylene)-2-(4-fluoro-3-trifluoro-methylbenzoyl)-1,3,4,9-tetrahydro-2,9-diazafluorene;

103 1,1-(3-dimethylamino-3-(3-fluorophenyl)pentamethylene)-2-(4-nitrobenzoyl)-1,3,4,9-tetrahydro-2,9-diazafluorene;

104 1,1-(3-dimethylamino-3-phenylpentamethylene)-2-(3,5-difluorobenzoyl)-1,3,4,9-tetrahydro-2,9-diazafluorene;

105 1,1-(3-dimethylamino-3-benzylpentamethylene)-2-(2-trifluoromethylbenzoyl)-1,3,4,9-tetrahydro-2,9-diazafluorene;

106 1,1-(3-dimethylamino-3-(3-fluorophenyl)pentamethylene)-2-(3,4-difluorobenzoyl)-1,3,4,9-tetrahydro-2,9-diazafluorene;

107 1,1-(3-dimethylamino-3-phenylpentamethylene)-2-(4-chlorobenzoyl)-1,3,4,9-tetrahydro-2,9-diazafluorene;

108 1,1-(3-dimethylamino-3-(3-fluorophenyl)pentamethylene)-2-(3-methylbenzoyl)-1,3,4,9-tetrahydro-2,9-diazafluorene;

109 1,1-(3-dimethylamino-3-(3-fluorophenyl)pentamethylene)-2-(2,3,4,5-tetrafluorobenzoyl)-1,3,4,9-tetrahydro-2,9-diazafluorene;
110 1,1-(3-dimethylamino-3-(3-fluorophenyl)pentamethylene)-2-(2,6-difluorobenzoyl)-1,3,4,9-tetrahydro-2,9-diazafluorene;
111 1,1-(3-dimethylamino-3-phenylpentamethylene)-2-(2-furylcarbonyl)-1,3,4,9-tetrahydro-2,9-diazafluorene;
112 1,1-(3-dimethylamino-3-(3-fluorophenyl)pentamethylene)-2-(2,4-dichlorobenzoyl)-1,3,4,9-tetrahydro-2,9-diazafluorene;
113 1,1-(3-dimethylamino-3-(3-fluorophenyl)pentamethylene)-2-(3-methoxycarbonylpropanoyl)-1,3,4,9-tetrahydro-2,9-diazafluorene;
114 1,1-(3-dimethylamino-3-(3-fluorophenyl)pentamethylene)-2-(3-chlorobenzoyl)-1,3,4,9-tetrahydro-2,9-diazafluorene;
115 1,1-(3-dimethylamino-3-(3-fluorophenyl)pentamethylene)-2-(2-fluoro-5-trifluoromethylbenzoyl)-1,3,4,9-tetrahydro-2,9-diazafluorene;
116 1,1-(3-dimethylamino-3-(3-fluorophenyl)pentamethylene)-2-(2-fluoro-4-trifluoromethylbenzoyl)-1,3,4,9-tetrahydro-2,9-diazafluorene;
117 1,1-(3-dimethylamino-3-benzylpentamethylene)-2-(2-thienylacetyl)-1,3,4,9-tetrahydro-2,9-diazafluorene;
118 1,1-(3-dimethylamino-3-benzylpentamethylene)-2-(2,6-dichlorobenzoyl)-1,3,4,9-tetrahydro-2,9-diazafluorene;
119 1,1-(3-dimethylamino-3-phenylpentamethylene)-2-(3,4-difluorobenzoyl)-1,3,4,9-tetrahydro-2,9-diazafluorene;
120 1,1-(3-dimethylamino-3-benzylpentamethylene)-2-(3-methylbenzoyl)-1,3,4,9-tetrahydro-2,9-diazafluorene;
121 1,1-(3-dimethylamino-3-phenylpentamethylene)-2-(3-methoxycarbonylpropanoyl)-1,3,4,9-tetrahydro-2,9-diazafluorene;
122 1,1-(3-dimethylamino-3-(3-fluorophenyl)pentamethylene)-2-(2-fluoro-6-trifluoromethylbenzoyl)-1,3,4,9-tetrahydro-2,9-diazafluorene;
123 1,1-(3-dimethylamino-3-phenylpentamethylene)-2-(2-methylbenzoyl)-1,3,4,9-tetrahydro-2,9-diazafluorene;
124 1,1-(3-dimethylamino-3-phenylpentamethylene)-2-(3,5-dichlorobenzoyl)-1,3,4,9-tetrahydro-2,9-diazafluorene;
125 1,1-(3-dimethylamino-3-benzylpentamethylene)-2-(2-furylcarbonyl)-1,3,4,9-tetrahydro-2,9-diazafluorene;
126 1,1-(3-dimethylamino-3-benzylpentamethylene)-2-(pentanoyl)-1,3,4,9-tetrahydro-2,9-diazafluorene;
127 1,1-(3-dimethylamino-3-benzylpentamethylene)-2-(6-fluoro-2-trifluoromethylbenzoyl)-1,3,4,9-tetrahydro-2,9-diazafluorene;
128 1,1-(3-dimethylamino-3-(3-fluorophenyl)pentamethylene)-2-(3-methoxybenzoyl)-1,3,4,9-tetrahydro-2,9-diazafluorene;
129 1,1-(3-dimethylamino-3-benzylpentamethylene)-2-(4-tert.butylbenzoyl)-1,3,4,9-tetrahydro-2,9-diazafluorene;
130 1,1-(3-dimethylamino-3-benzylpentamethylene)-2-(phenylacetyl)-1,3,4,9-tetrahydro-2,9-diazafluorene;
131 1,1-(3-dimethylamino-3-(3-fluorophenyl)pentamethylene)-2-(3,5-dichlorobenzoyl)-1,3,4,9-tetrahydro-2,9-diazafluorene;
132 1,1-(3-dimethylamino-3-benzylpentamethylene)-2-(2,3,4,5,6-pentafluorobenzoyl)-1,3,4,9-tetrahydro-2,9-diazafluorene;
133 1,1-(3-dimethylamino-3-benzylpentamethylene)-2-(3-nitrobenzoyl)-1,3,4,9-tetrahydro-2,9-diazafluorene;
134 1,1-(3-dimethylamino-3-phenylpentamethylene)-2-(3-nitrobenzoyl)-1,3,4,9-tetrahydro-2,9-diazafluorene;
135 1,1-(3-dimethylamino-3-benzylpentamethylene)-2-(2,3,4,5-tetrafluorobenzoyl)-1,3,4,9-tetrahydro-2,9-diazafluorene;
136 1,1-(3-dimethylamino-3-phenylpentamethylene)-2-(2-thienylacetyl)-1,3,4,9-tetrahydro-2,9-diazafluorene;
137 1,1-(3-dimethylamino-3-phenylpentamethylene)-2-(2-fluoro-4-trifluoromethylbenzoyl)-1,3,4,9-tetrahydro-2,9-diazafluorene;
138 1,1-(3-dimethylamino-3-phenylpentamethylene)-2-(2-fluorobenzoyl)-1,3,4,9-tetrahydro-2,9-diazafluorene;
139 1,1-(3-dimethylamino-3-phenylpentamethylene)-2-(cyclobutylcarbonyl)-1,3,4,9-tetrahydro-2,9-diazafluorene;
140 1,1-(3-dimethylamino-3-phenylpentamethylene)-2-(2-methoxybenzoyl)-1,3,4,9-tetrahydro-2,9-diazafluorene;
141 1,1-(3-dimethylamino-3-phenylpentamethylene)-2-(2,5-difluorobenzoyl)-1,3,4,9-tetrahydro-2,9-diazafluorene;
142 1,1-(3-dimethylamino-3-(3-fluorophenyl)pentamethylene)-2-(2-bromobenzoyl)-1,3,4,9-tetrahydro-2,9-diazafluorene;
143 1,1-(3-dimethylamino-3-phenylpentamethylene)-2-(3-fluoro-5-trifluoromethylbenzoyl)-1,3,4,9-tetrahydro-2,9-diazafluorene;
144 1,1-(3-dimethylamino-3-phenylpentamethylene)-2-(2-fluoro-5-trifluoromethylbenzoyl)-1,3,4,9-tetrahydro-2,9-diazafluorene;
145 1,1-(3-dimethylamino-3-phenylpentamethylene)-2-(2,3-difluorobenzoyl)-1,3,4,9-tetrahydro-2,9-diazafluorene, and physiologically compatible salts thereof.

It has been found that spirocyclic cyclohexane derivatives in which W denotes $NR^4$ and X denotes $NR^{17}$ are particularly advantageous. Accordingly it is preferred to use compounds in which R denotes $NR^4$ and X denotes $NR^{17}$. It is particularly preferred to use compounds selected from the group consisting of:

2 1,1-(3-dimethylamino-3-benzylpentamethylene)-2-(2-nitrobenzoyl)-1,3,4,9-tetrahydro-2,9-diazafluorene;
8 1,1-(3-dimethylamino-3-phenylpentamethylene)-3-hydroxymethyl-1,3,4,9-tetrahydro-2,9-diazafluorene;
9 1,1-(3-dimethylamino-3-phenylpentamethylene)-2-(2,3,4,5,6-pentafluorobenzoyl)-1,3,4,9-tetrahydro-2,9-diazafluorene;
10 1,1-(3-dimethylamino-3-phenylpentamethylene)-2-(methoxycarbonyl)-1,3,4,9-tetrahydro-2,9-diazafluorene;
11 1,1-(3-dimethylamino-3-phenylpentamethylene)-7-fluoro-1,3,4,9-tetrahydro-2,9-diazafluorene;
13 1,1-(3-dimethylamino-3-(3-fluorophenyl)pentamethylene)-1,3,4,9-tetrahydro-2,9-diazafluorene;
14 1,1-(3-dimethylamino-3-phenylpentamethylene)-2-acetyl-1,3,4,9-tetrahydro-2,9-diazafluorene;
17 1,1-(3-dimethylamino-3-(2-pyridyl)pentamethylene)-1,3,4,9-tetrahydro-2,9-diazafluorene;
19 1,1-(3-dimethylamino-3-phenylpentamethylene)-2-acetyl-7-fluoro-1,3,4,9-tetrahydro-2,9-diazafluorene;
20 1,1-(3-dimethylamino-3-phenylpentamethylene)-1,3,4,9-tetrahydro-2,9-diazafluorene;
25 1,1-(3-dimethylamino-3-(4-fluorophenyl)pentamethylene)-1,3,4,9-tetrahydro-2,9-diazafluorene;
26 1,1-(3-dimethylamino-3-phenylpentamethylene)-3-methyl-1,3,4,9-tetrahydro-2,9-diazafluorene;
30 1,1-(3-dimethylamino-3-phenylpentamethylene)-3-methyl-1,3,4,9-tetrahydro-2,9-diazafluorene;
37 1,1-(3-dimethylamino-3-(4-fluorophenyl)pentamethylene)-2-acetyl-1,3,4,9-tetrahydro-2,9-diazafluorene;
38 1,1-(3-dimethylamino-3-benzylpentamethylene)-1,3,4,9-tetrahydro-2,9-diazafluorene;

39 1,1-(3-dimethylamino-3-phenylpentamethylene)-6-fluoro-1,3,4,9-tetrahydro-2,9-diazafluorene;

40 1,1-(3-dimethylamino-3-phenylpentamethylene)-6-methyl-1,3,4,9-tetrahydro-2,9-diazafluorene;

50 1,1-(3-dimethylamino-3-(fluorophenyl)pentamethylene)-2-cinnamoyl-1,3,4,9-tetrahydro-2,9-diazafluorene;

51 1,1-(3-dimethylamino-3-(fluorophenyl)pentamethylene)-2-(3,3-dimethylbutanoyl)-1,3,4,9-tetrahydro-2,9-diazafluorene;

52 1,1-(3-dimethylamino-3-(fluorophenyl)pentamethylene)-2-(cyclopentylcarbonyl)-1,3,4,9-tetrahydro-2,9-diazafluorene;

53 1,1-(3-dimethylamino-3-phenylpentamethylene)-2-(3,3-dimethylbutanoyl)-1,3,4,9-tetrahydro-2,9-diazafluorene;

54 1,1-(3-dimethylamino-3-(fluorophenyl)pentamethylene)-2-(pentanoyl)-1,3,4,9-tetrahydro-2,9-diazafluorene;

55 1,1-(3-dimethylamino-3-(fluorophenyl)pentamethylene)-2-(2-furylcarbonyl)-1,3,4,9-tetrahydro-2,9-diazafluorene;

56 1,1-(3-dimethylamino-3-phenylpentamethylene)-2-(2-furylcarbonyl)-1,3,4,9-tetrahydro-2,9-diazafluorene;

57 1,1-(3-dimethylamino-3-(fluorophenyl)pentamethylene)-2-(4-fluorobenzoyl)-1,3,4,9-tetrahydro-2,9-diazafluorene;

58 1,1-(3-dimethylamino-3-(fluorophenyl)pentamethylene)-2-(2-methoxybenzoyl)-1,3,4,9-tetrahydro-2,9-diazafluorene;

59 1,1-(3-dimethylamino-3-phenylpentamethylene)-2-(3-methylbutanoyl)-1,3,4,9-tetrahydro-2,9-diazafluorene;

60 1,1-(3-dimethylamino-3-(fluorophenyl)pentamethylene)-2-(cyclohexylcarbonyl)-1,3,4,9-tetrahydro-2,9-diazafluorene;

61 1,1-(3-dimethylamino-3-(fluorophenyl)pentamethylene)-2-benzoyl-1,3,4,9-tetrahydro-2,9-diazafluorene;

62 1,1-(3-dimethylamino-3-phenylpentamethylene)-2-(cyclohexylcarbonyl)-1,3,4,9-tetrahydro-2,9-diazafluorene;

63 1,1-(3-dimethylamino-3-(fluorophenyl)pentamethylene)-2-(phenylacetyl)-1,3,4,9-tetrahydro-2,9-diazafluorene;

64 1,1-(3-dimethylamino-3-(fluorophenyl)pentamethylene)-2-(4-methoxybenzoyl)-1,3,4,9-tetrahydro-2,9-diazafluorene;

65 1,1-(3-dimethylamino-3-phenylpentamethylene)-2-(4-trifluoromethylbenzoyl)-1,3,4,9-tetrahydro-2,9-diazafluorene;

66 1,1-(3-dimethylamino-3-(fluorophenyl)pentamethylene)-2-(thien-2-ylacetyl)-1,3,4,9-tetrahydro-2,9-diazafluorene;

67 1,1-(3-dimethylamino-3-(fluorophenyl)pentamethylene)-2-(phenylacetyl)-1,3,4,9-tetrahydro-2,9-diazafluorene;

68 1,1-(3-dimethylamino-3-(fluorophenyl)pentamethylene)-2-butanoyl-1,3,4,9-tetrahydro-2,9-diazafluorene;

69 1,1-(3-dimethylamino-3-benzylpentamethylene)-2-(4-trifluoromethylbenzoyl)-1,3,4,9-tetrahydro-2,9-diazafluorene;

70 1,1-(3-dimethylamino-3-benzylpentamethylene)-2-(3-fluoro-5-trifluoromethylbenzoyl)-1,3,4,9-tetrahydro-2,9-diazafluorene;

71 1,1-(3-dimethylamino-3-(fluorophenyl)pentamethylene)-2-(2,3-difluorobenzoyl)-1,3,4,9-tetrahydro-2,9-diazafluorene;

72 1,1-(3-dimethylamino-3-(fluorophenyl)pentamethylene)-2-(4-methylbenzoyl)-1,3,4,9-tetrahydro-2,9-diazafluorene;

73 1,1-(3-dimethylamino-3-phenylpentamethylene)-2-(3-phenylpropanoyl)-1,3,4,9-tetrahydro-2,9-diazafluorene;

74 1,1-(3-dimethylamino-3-phenylpentamethylene)-2-(3,4-dichlorobenzoyl)-1,3,4,9-tetrahydro-2,9-diazafluorene;

75 1,1-(3-dimethylamino-3-benzylpentamethylene)-2-cinnamoyl-1,3,4,9-tetrahydro-2,9-diazafluorene;

76 1,1-(3-dimethylamino-3-benzylpentamethylene)-2-(2,6-difluorobenzoyl)-1,3,4,9-tetrahydro-2,9-diazafluorene;

77 1,1-(3-dimethylamino-3-phenylpentamethylene)-2-(3-methoxycarbonylpropanoyl)-1,3,4,9-tetrahydro-2,9-diazafluorene;

78 1,1-(3-dimethylamino-3-(fluorophenyl)pentamethylene)-2-(3-chlorobenzoyl)-1,3,4,9-tetrahydro-2,9-diazafluorene;

79 1,1-(3-dimethylamino-3-phenylpentamethylene)-2-(3-fluorobenzoyl)-1,3,4,9-tetrahydro-2,9-diazafluorene;

80 1,1-(3-dimethylamino-3-phenylpentamethylene)-2-(2,6-difluorobenzoyl)-1,3,4,9-tetrahydro-2,9-diazafluorene;

81 1,1-(3-dimethylamino-3-(fluorophenyl)pentamethylene)-2-(3,4-dichlorobenzoyl)-1,3,4,9-tetrahydro-2,9-diazafluorene;

82 1,1-(3-dimethylamino-3-benzylpentamethylene)-2-(2,3,4,5,6-pentafluorobenzoyl)-1,3,4,9-tetrahydro-2,9-diazafluorene;

83 1,1-(3-dimethylamino-3-benzylpentamethylene)-2-cyclohexylcarbonyl-1,3,4,9-tetrahydro-2,9-diazafluorene;

84 1,1-(3-dimethylamino-3-phenylpentamethylene)-2-(3-cyclopentylpropanoyl)-1,3,4,9-tetrahydro-2,9-diazafluorene;

85 1,1-(3-dimethylamino-3-(fluorophenyl)pentamethylene)-2-(4-fluoro-3-trifluoromethylbenzoyl)-1,3,4,9-tetrahydro-2,9-diazafluorene;

86 1,1-(3-dimethylamino-3-(fluorophenyl)pentamethylene)-2-(4-methylbenzoyl)-1,3,4,9-tetrahydro-2,9-diazafluorene;

87 1,1-(3-dimethylamino-3-(fluorophenyl)pentamethylene)-2-(3,4,5-trimethoxybenzoyl)-1,3,4,9-tetrahydro-2,9-diazafluorene;

88 1,1-(3-dimethylamino-3-benzylpentamethylene)-2-cyclobutylcarbonyl-1,3,4,9-tetrahydro-2,9-diazafluorene;

89 1,1-(3-dimethylamino-3-benzylpentamethylene)-2-(2,6-dichlorobenzoyl)-1,3,4,9-tetrahydro-2,9-diazafluorene;

90 1,1-(3-dimethylamino-3-(fluorophenyl)pentamethylene)-2-(3-methoxybenzoyl)-1,3,4,9-tetrahydro-2,9-diazafluorene;

91 1,1-(3-dimethylamino-3-phenylpentamethylene)-2-(2-thienylcarbonyl)-1,3,4,9-tetrahydro-2,9-diazafluorene;

92 1,1-(3-dimethylamino-3-(fluorophenyl)pentamethylene)-2-propanoyl-1,3,4,9-tetrahydro-2,9-diazafluorene;

93 1,1-(3-dimethylamino-3-(fluorophenyl)pentamethylene)-2-(2,4-difluorobenzoyl)-1,3,4,9-tetrahydro-2,9-diazafluorene;

94 1,1-(3-dimethylamino-3-(fluorophenyl)pentamethylene)-2-(3,5-difluorobenzoyl)-1,3,4,9-tetrahydro-2,9-diazafluorene;

95 1,1-(3-dimethylamino-3-(fluorophenyl)pentamethylene)-2-(4-tert.butylbenzoyl)-1,3,4,9-tetrahydro-2,9-diazafluorene;

96 1,1-(3-dimethylamino-3-benzylpentamethylene)-2-(3-methoxycarbonylpropanoyl)-1,3,4,9-tetrahydro-2,9-diazafluorene;

97 1,1-(3-dimethylamino-3-(fluorophenyl)pentamethylene)-2-(3,4-difluorobenzoyl)-1,3,4,9-tetrahydro-2,9-diazafluorene;

98 1,1-(3-dimethylamino-3-phenylpentamethylene)-2-(2-ethylhexanoyl)-1,3,4,9-tetrahydro-2,9-diazafluorene;

99 1,1-(3-dimethylamino-3-(fluorophenyl)pentamethylene)-2-(2-methylbenzoyl)-1,3,4,9-tetrahydro-2,9-diazafluorene;

100  1,1-(3-dimethylamino-3-phenylpentamethylene)-2-(3-phenylpropanoyl)-1,3,4,9-tetrahydro-2,9-diazafluorene;
101  1,1-(3-dimethylamino-3-(3-fluorophenyl)pentamethylene)-2-(3-fluoro-5-trifluoromethylbenzoyl)-1,3,4,9-tetrahydro-2,9-diazafluorene;
102  1,1-(3-dimethylamino-3-phenylpentamethylene)-2-(4-fluoro-3-trifluoro-methylbenzoyl)-1,3,4,9-tetrahydro-2,9-diazafluorene;
103  1,1-(3-dimethylamino-3-(3-fluorophenyl)pentamethylene)-2-(4-nitrobenzoyl)-1,3,4,9-tetrahydro-2,9-diazafluorene;
104  1,1-(3-dimethylamino-3-phenylpentamethylene)-2-(3,5-difluorobenzoyl)-1,3,4,9-tetrahydro-2,9-diazafluorene;
105  1,1-(3-dimethylamino-3-benzylpentamethylene)-2-(2-trifluoromethylbenzoyl)-1,3,4,9-tetrahydro-2,9-diazafluorene;
106  1,1-(3-dimethylamino-3-(3-fluorophenyl)pentamethylene)-2-(3,4-difluorobenzoyl)-1,3,4,9-tetrahydro-2,9-diazafluorene;
107  1,1-(3-dimethylamino-3-phenylpentamethylene)-2-(4-chlorobenzoyl)-1,3,4,9-tetrahydro-2,9-diazafluorene;
108  1,1-(3-dimethylamino-3-(3-fluorophenyl)pentamethylene)-2-(3-methylbenzoyl)-1,3,4,9-tetrahydro-2,9-diazafluorene;
109  1,1-(3-dimethylamino-3-(3-fluorophenyl)pentamethylene)-2-(2,3,4,5-tetrafluorobenzoyl)-1,3,4,9-tetrahydro-2,9-diazafluorene;
110  1,1-(3-dimethylamino-3-(3-fluorophenyl)pentamethylene)-2-(2,6-difluorobenzoyl)-1,3,4,9-tetrahydro-2,9-diazafluorene;
111  1,1-(3-dimethylamino-3-phenylpentamethylene)-2-(2-furylcarbonyl)-1,3,4,9-tetrahydro-2,9-diazafluorene;
112  1,1-(3-dimethylamino-3-(3-fluorophenyl)pentamethylene)-2-(2,4-dichlorobenzoyl)-1,3,4,9-tetrahydro-2,9-diazafluorene;
113  1,1-(3-dimethylamino-3-(3-fluorophenyl)pentamethylene)-2-(3-methoxycarbonylpropanoyl)-1,3,4,9-tetrahydro-2,9-diazafluorene;
114  1,1-(3-dimethylamino-3-(3-fluorophenyl)pentamethylene)-2-(3-chlorobenzoyl)-1,3,4,9-tetrahydro-2,9-diazafluorene;
115  1,1-(3-dimethylamino-3-(3-fluorophenyl)pentamethylene)-2-(2-fluoro-5-trifluoromethylbenzoyl)-1,3,4,9-tetrahydro-2,9-diazafluorene;
116  1,1-(3-dimethylamino-3-(3-fluorophenyl)pentamethylene)-2-(2-fluoro-4-trifluoro-methylbenzoyl)-1,3,4,9-tetrahydro-2,9-diazafluorene;
117  1,1-(3-dimethylamino-3-benzylpentamethylene)-2-(2-thienylacetyl)-1,3,4,9-tetrahydro-2,9-diazafluorene;
118  1,1-(3-dimethylamino-3-benzylpentamethylene)-2-(2,6-dichlorobenzoyl)-1,3,4,9-tetrahydro-2,9-diazafluorene;
119  1,1-(3-dimethylamino-3-phenylpentamethylene)-2-(3,4-difluorobenzoyl)-1,3,4,9-tetrahydro-2,9-diazafluorene;
120  1,1-(3-dimethylamino-3-benzylpentamethylene)-2-(3-methylbenzoyl)-1,3,4,9-tetrahydro-2,9-diazafluorene;
121  1,1-(3-dimethylamino-3-benzylpentamethylene)-2-(3-methoxycarbonylpropanoyl)-1,3,4,9-tetrahydro-2,9-diazafluorene;
122  1,1-(3-dimethylamino-3-(3-fluorophenyl)pentamethylene)-2-(2-fluoro-6-trifluoromethylbenzoyl)-1,3,4,9-tetrahydro-2,9-diazafluorene;
123  1,1-(3-dimethylamino-3-phenylpentamethylene)-2-(2-methylbenzoyl)-1,3,4,9-tetrahydro-2,9-diazafluorene;
124  1,1-(3-dimethylamino-3-phenylpentamethylene)-2-(3,5-dichlorobenzoyl)-1,3,4,9-tetrahydro-2,9-diazafluorene;
125  1,1-(3-dimethylamino-3-benzylpentamethylene)-2-(2-furylcarbonyl)-1,3,4,9-tetrahydro-2,9-diazafluorene;
126  1,1-(3-dimethylamino-3-benzylpentamethylene)-2-(pentanoyl)-1,3,4,9-tetrahydro-2,9-diazafluorene;
127  1,1-(3-dimethylamino-3-benzylpentamethylene)-2-(6-fluoro-2-trifluoromethylbenzoyl)-1,3,4,9-tetrahydro-2,9-diazafluorene;
128  1,1-(3-dimethylamino-3-(3-fluorophenyl)pentamethylene)-2-(3-methoxybenzoyl)-1,3,4,9-tetrahydro-2,9-diazafluorene;
129  1,1-(3-dimethylamino-3-benzylpentamethylene)-2-(4-tert.butylbenzoyl)-1,3,4,9-tetrahydro-2,9-diazafluorene;
130  1,1-(3-dimethylamino-3-benzylpentamethylene)-2-(phenylacetyl)-1,3,4,9-tetrahydro-2,9-diazafluorene;
131  1,1-(3-dimethylamino-3-(3-fluorophenyl)pentamethylene)-2-(3,5-dichlorobenzoyl)-1,3,4,9-tetrahydro-2,9-diazafluorene;
132  1,1-(3-dimethylamino-3-benzylpentamethylene)-2-(2,3,4,5,6-pentafluorobenzoyl)-1,3,4,9-tetrahydro-2,9-diazafluorene;
133  1,1-(3-dimethylamino-3-benzylpentamethylene)-2-(3-nitrobenzoyl)-1,3,4,9-tetrahydro-2,9-diazafluorene;
134  1,1-(3-dimethylamino-3-phenylpentamethylene)-2-(3-nitrobenzoyl)-1,3,4,9-tetrahydro-2,9-diazafluorene;
135  1,1-(3-dimethylamino-3-benzylpentamethylene)-2-(2,3,4,5-tetrafluorobenzoyl)-1,3,4,9-tetrahydro-2,9-diazafluorene;
136  1,1-(3-dimethylamino-3-phenylpentamethylene)-2-(2-thienylacetyl)-1,3,4,9-tetrahydro-2,9-diazafluorene;
137  1,1-(3-dimethylamino-3-phenylpentamethylene)-2-(2-fluoro-4-trifluoromethylbenzoyl)-1,3,4,9-tetrahydro-2,9-diazafluorene;
138  1,1-(3-dimethylamino-3-phenylpentamethylene)-2-(2-fluorobenzoyl)-1,3,4,9-tetrahydro-2,9-diazafluorene;
139  1,1-(3-dimethylamino-3-phenylpentamethylene)-2-(cyclobutylcarbonyl)-1,3,4,9-tetrahydro-2,9-diazafluorene;
140  1,1-(3-dimethylamino-3-phenylpentamethylene)-2-(2-methoxybenzoyl)-1,3,4,9-tetrahydro-2,9-diazafluorene;
141  1,1-(3-dimethylamino-3-phenylpentamethylene)-2-(2,5-difluorobenzoyl)-1,3,4,9-tetrahydro-2,9-diazafluorene;
142  1,1-(3-dimethylamino-3-(3-fluorophenyl)pentamethylene)-2-(2-bromobenzoyl)-1,3,4,9-tetrahydro-2,9-diazafluorene;
143  1,1-(3-dimethylamino-3-phenylpentamethylene)-2-(3-fluoro-5-trifluoromethylbenzoyl)-1,3,4,9-tetrahydro-2,9-diazafluorene;
144  1,1-(3-dimethylamino-3-phenylpentamethylene)-2-(2-fluoro-5-trifluoromethylbenzoyl)-1,3,4,9-tetrahydro-2,9-diazafluorene;
145  1,1-(3-dimethylamino-3-phenylpentamethylene)-2-(2,3-difluorobenzoyl)-1,3,4,9-tetrahydro-2,9-diazafluorene, and physiologically compatible salts thereof.

Particularly preferred compounds are selected from the group consisting of:

8  1,1-(3-dimethylamino-3-phenylpentamethylene)-3-hydroxymethyl-1,3,4,9-tetrahydro-2,9-diazafluorene;
10  1,1-(3-dimethylamino-3-phenylpentamethylene)-2-(methoxycarbonyl)-1,3,4,9-tetrahydro-2,9-diazafluorene;
11  1,1-(3-dimethylamino-3-phenylpentamethylene)-7-fluoro-1,3,4,9-tetrahydro-2,9-diazafluorene;
13  1,1-(3-dimethylamino-3-(3-fluorophenyl)pentamethylene)-1,3,4,9-tetrahydro-2,9-diazafluorene;
14  1,1-(3-dimethylamino-3-phenylpentamethylene)-2-acetyl-1,3,4,9-tetrahydro-2,9-diazafluorene;
17 1,1-(3-dimethylamino-3-(2-pyridyl)pentamethylene)-1,3,4,9-tetrahydro-2,9-diazafluorene;
19  1,1-(3-dimethylamino-3-phenylpentamethylene)-2-acetyl-7-fluoro-1,3,4,9-tetrahydro-2,9-diazafluorene;

20 1,1-(3-dimethylamino-3-phenylpentamethylene)-1,3,4,9-tetrahydro-2,9-diazafluorene;
25 1,1-(3-dimethylamino-3-(4-fluorophenyl)pentamethylene)-1,3,4,9-tetrahydro-2,9-diazafluorene;
50 1,1-(3-dimethylamino-3-(3-fluorophenyl)pentamethylene)-2-cinnamoyl-1,3,4,9-tetrahydro-2,9-diazafluorene;
51 1,1-(3-dimethylamino-3-(3-fluorophenyl)pentamethylene)-2-(3,3-dimethylbutanoyl)-1,3,4,9-tetrahydro-2,9-diazafluorene;
52 1,1-(3-dimethylamino-3-(3-fluorophenyl)pentamethylene)-2-(cyclopentylcarbonyl)-1,3,4,9-tetrahydro-2,9-diazafluorene;
53 1,1-(3-dimethylamino-3-phenylpentamethylene)-2-(3,3-dimethylbutanoyl)-1,3,4,9-tetrahydro-2,9-diazafluorene;
54 1,1-(3-dimethylamino-3-(3-fluorophenyl)pentamethylene)-2-(pentanoyl)-1,3,4,9-tetrahydro-2,9-diazafluorene;
55 1,1-(3-dimethylamino-3-(3-fluorophenyl)pentamethylene)-2-(2-furylcarbonyl)-1,3,4,9-tetrahydro-2,9-diazafluorene;
56 1,1-(3-dimethylamino-3-phenylpentamethylene)-2-(2-furylcarbonyl)-1,3,4,9-tetrahydro-2,9-diazafluorene;
57 1,1-(3-dimethylamino-3-(3-fluorophenyl)pentamethylene)-2-(4-fluorobenzoyl)-1,3,4,9-tetrahydro-2,9-diazafluorene;
58 1,1-(3-dimethylamino-3-(3-fluorophenyl)pentamethylene)-2-(2-methoxybenzoyl)-1,3,4,9-tetrahydro-2,9-diazafluorene;
59 1,1-(3-dimethylamino-3-phenylpentamethylene)-2-(3-methylbutanoyl)-1,3,4,9-tetrahydro-2,9-diazafluorene;
60 1,1-(3-dimethylamino-3-(3-fluorophenyl)pentamethylene)-2-(cyclohexylcarbonyl)-1,3,4,9-tetrahydro-2,9-diazafluorene;
61 1,1-(3-dimethylamino-3-(3-fluorophenyl)pentamethylene)-2-benzoyl-1,3,4,9-tetrahydro-2,9-diazafluorene;
62 1,1-(3-dimethylamino-3-phenylpentamethylene)-2-(cyclohexylcarbonyl)-1,3,4,9-tetrahydro-2,9-diazafluorene;
63 1,1-(3-dimethylamino-3-(3-fluorophenyl)pentamethylene)-2-(phenylacetyl)-1,3,4,9-tetrahydro-2,9-diazafluorene;
64 1,1-(3-dimethylamino-3-(3-fluorophenyl)pentamethylene)-2-(4-methoxybenzoyl)-1,3,4,9-tetrahydro-2,9-diazafluorene;
65 1,1-(3-dimethylamino-3-phenylpentamethylene)-2-(4-trifluoromethylbenzoyl)-1,3,4,9-tetrahydro-2,9-diazafluorene;
66 1,1-(3-dimethylamino-3-(3-fluorophenyl)pentamethylene)-2-(thien-2-ylacetyl)-1,3,4,9-tetrahydro-2,9-diazafluorene;
67 1,1-(3-dimethylamino-3-(3-fluorophenyl)pentamethylene)-2-(phenylacetyl)-1,3,4,9-tetrahydro-2,9-diazafluorene;
68 1,1-(3-dimethylamino-3-(3-fluorophenyl)pentamethylene)-2-butanoyl-1,3,4,9-tetrahydro-2,9-diazafluorene;
69 1,1-(3-dimethylamino-3-benzylpentamethylene)-2-(4-trifluoromethylbenzoyl)-1,3,4,9-tetrahydro-2,9-diazafluorene;
70 1,1-(3-dimethylamino-3-benzylpentamethylene)-2-(3-fluoro-5-trifluoromethylbenzoyl)-1,3,4,9-tetrahydro-2,9-diazafluorene;
71 1,1-(3-dimethylamino-3-(3-fluorophenyl)pentamethylene)-2-(2,3-difluorobenzoyl)-1,3,4,9-tetrahydro-2,9-diazafluorene;
72 1,1-(3-dimethylamino-3-(3-fluorophenyl)pentamethylene)-2-(4-methylbenzoyl)-1,3,4,9-tetrahydro-2,9-diazafluorene;
73 1,1-(3-dimethylamino-3-phenylpentamethylene)-2-(3-phenylpropanoyl)-1,3,4,9-tetrahydro-2,9-diazafluorene;
74 1,1-(3-dimethylamino-3-phenylpentamethylene)-2-(3,4-dichlorobenzoyl)-1,3,4,9-tetrahydro-2,9-diazafluorene;
75 1,1-(3-dimethylamino-3-benzylpentamethylene)-2-cinnamoyl-1,3,4,9-tetrahydro-2,9-diazafluorene;
76 1,1-(3-dimethylamino-3-benzylpentamethylene)-2-(2,6-difluorobenzoyl)-1,3,4,9-tetrahydro-2,9-diazafluorene;
77 1,1-(3-dimethylamino-3-phenylpentamethylene)-2-(3-methoxycarbonylpropanoyl)-1,3,4,9-tetrahydro-2,9-diazafluorene;
78 1,1-(3-dimethylamino-3-(3-fluorophenyl)pentamethylene)-2-(3-chlorobenzoyl)-1,3,4,9-tetrahydro-2,9-diazafluorene;
79 1,1-(3-dimethylamino-3-phenylpentamethylene)-2-(3-fluorobenzoyl)-1,3,4,9-tetrahydro-2,9-diazafluorene;
80 1,1-(3-dimethylamino-3-phenylpentamethylene)-2-(2,6-difluorobenzoyl)-1,3,4,9-tetrahydro-2,9-diazafluorene;
81 1,1-(3-dimethylamino-3-(3-fluorophenyl)pentamethylene)-2-(3,4-dichlorobenzoyl)-1,3,4,9-tetrahydro-2,9-diazafluorene;
82 1,1-(3-dimethylamino-3-benzylpentamethylene)-2-(2,3,4,5,6-pentafluorobenzoyl)-1,3,4,9-tetrahydro-2,9-diazafluorene;
83 1,1-(3-dimethylamino-3-benzylpentamethylene)-2-cyclohexylcarbonyl-1,3,4,9-tetrahydro-2,9-diazafluorene;
84 1,1-(3-dimethylamino-3-phenylpentamethylene)-2-(3-cyclopentylpropanoyl)-1,3,4,9-tetrahydro-2,9-diazafluorene;
85 1,1-(3-dimethylamino-3-(3-fluorophenyl)pentamethylene)-2-(4-fluoro-3-trifluoromethylbenzoyl)-1,3,4,9-tetrahydro-2,9-diazafluorene;
86 1,1-(3-dimethylamino-3-(3-fluorophenyl)pentamethylene)-2-(4-methylbenzoyl)-1,3,4,9-tetrahydro-2,9-diazafluorene;
87 1,1-(3-dimethylamino-3-(3-fluorophenyl)pentamethylene)-2-(3,4,5-trimethoxybenzoyl)-1,3,4,9-tetrahydro-2,9-diazafluorene;
88 1,1-(3-dimethylamino-3-benzylpentamethylene)-2-cyclobutylcarbonyl-1,3,4,9-tetrahydro-2,9-diazafluorene;
89 1,1-(3-dimethylamino-3-benzylpentamethylene)-2-(2,6-dichlorobenzoyl)-1,3,4,9-tetrahydro-2,9-diazafluorene;
90 1,1-(3-dimethylamino-3-(3-fluorophenyl)pentamethylene)-2-(3-methoxybenzoyl)-1,3,4,9-tetrahydro-2,9-diazafluorene;
91 1,1-(3-dimethylamino-3-phenylpentamethylene)-2-(2-thienylcarbonyl)-1,3,4,9-tetrahydro-2,9-diazafluorene;
92 1,1-(3-dimethylamino-3-(3-fluorophenyl)pentamethylene)-2-propanoyl-1,3,4,9-tetrahydro-2,9-diazafluorene;
93 1,1-(3-dimethylamino-3-(3-fluorophenyl)pentamethylene)-2-(2,4-difluorobenzoyl)-1,3,4,9-tetrahydro-2,9-diazafluorene;
94 1,1-(3-dimethylamino-3-(3-fluorophenyl)pentamethylene)-2-(3,5-difluorobenzoyl)-1,3,4,9-tetrahydro-2,9-diazafluorene;
95 1,1-(3-dimethylamino-3-(3-fluorophenyl)pentamethylene)-2-(4-tert.butylbenzoyl)-1,3,4,9-tetrahydro-2,9-diazafluorene;
96 1,1-(3-dimethylamino-3-benzylpentamethylene)-2-(3-methoxycarbonylpropanoyl)-1,3,4,9-tetrahydro-2,9-diazafluorene;
97 1,1-(3-dimethylamino-3-(3-fluorophenyl)pentamethylene)-2-(3,4-difluorobenzoyl)-1,3,4,9-tetrahydro-2,9-diazafluorene;
98 1,1-(3-dimethylamino-3-phenylpentamethylene)-2-(2-ethylhexanoyl)-1,3,4,9-tetrahydro-2,9-diazafluorene;
99 1,1-(3-dimethylamino-3-(3-fluorophenyl)pentamethylene)-2-(2-methylbenzoyl)-1,3,4,9-tetrahydro-2,9-diazafluorene;

100 1,1-(3-dimethylamino-3-phenylpentamethylene)-2-(3-phenylpropanoyl)-1,3,4,9-tetrahydro-2,9-diazafluorene;
101 1,1-(3-dimethylamino-3-(3-fluorophenyl)pentamethylene)-2-(3-fluoro-5-trifluoromethylbenzoyl)-1,3,4,9-tetrahydro-2,9-diazafluorene;
102 1,1-(3-dimethylamino-3-phenylpentamethylene)-2-(4-fluoro-3-trifluoro-methylbenzoyl)-1,3,4,9-tetrahydro-2,9-diazafluorene, and physiologically compatible salts thereof.

Particularly preferred are compounds selected from the group consisting of:
8 1,1-(3-dimethylamino-3-phenylpentamethylene)-3-hydroxymethyl-1,3,4,9-tetrahydro-2,9-diazafluorene;
10 1,1-(3-dimethylamino-3-phenylpentamethylene)-2-(methoxycarbonyl)-1,3,4,9-tetrahydro-2,9-diazafluorene;
11 1,1-(3-dimethylamino-3-phenylpentamethylene)-7-fluoro-1,3,4,9-tetrahydro-2,9-diazafluorene;
13 1,1-(3-dimethylamino-3-(3-fluorophenyl)pentamethylene)-1,3,4,9-tetrahydro-2,9-diazafluorene;
14 1,1-(3-dimethylamino-3-phenylpentamethylene)-2-acetyl-1,3,4,9-tetrahydro-2,9-diazafluorene;
17 1,1-(3-dimethylamino-3-(2-pyridyl)pentamethylene)-1,3,4,9-tetrahydro-2,9-diazafluorene;
50 1,1-(3-dimethylamino-3-(3-fluorophenyl)pentamethylene)-2-cinnamoyl-1,3,4,9-tetrahydro-2,9-diazafluorene;
51 1,1-(3-dimethylamino-3-(3-fluorophenyl)pentamethylene)-2-(3,3-dimethylbutanoyl)-1,3,4,9-tetrahydro-2,9-diazafluorene;
52 1,1-(3-dimethylamino-3-(3-fluorophenyl)pentamethylene)-2-(cyclopentylcarbonyl)-1,3,4,9-tetrahydro-2,9-diazafluorene;
53 1,1-(3-dimethylamino-3-phenylpentamethylene)-2-(3,3-dimethylbutanoyl)-1,3,4,9-tetrahydro-2,9-diazafluorene;
54 1,1-(3-dimethylamino-3-(3-fluorophenyl)pentamethylene)-2-(pentanoyl)-1,3,4,9-tetrahydro-2,9-diazafluorene;
55 1,1-(3-dimethylamino-3-(3-fluorophenyl)pentamethylene)-2-(2-furylcarbonyl)-1,3,4,9-tetrahydro-2,9-diazafluorene;
56 1,1-(3-dimethylamino-3-phenylpentamethylene)-2-(2-furylcarbonyl)-1,3,4,9-tetrahydro-2,9-diazafluorene;
57 1,1-(3-dimethylamino-3-(3-fluorophenyl)pentamethylene)-2-(4-fluorobenzoyl)-1,3,4,9-tetrahydro-2,9-diazafluorene;
58 1,1-(3-dimethylamino-3-(3-fluorophenyl)pentamethylene)-2-(2-methoxybenzoyl)-1,3,4,9-tetrahydro-2,9-diazafluorene;
59 1,1-(3-dimethylamino-3-phenylpentamethylene)-2-(3-methylbutanoyl)-1,3,4,9-tetrahydro-2,9-diazafluorene;
60 1,1-(3-dimethylamino-3-(3-fluorophenyl)pentamethylene)-2-(cyclohexylcarbonyl)-1,3,4,9-tetrahydro-2,9-diazafluorene;
61 1,1-(3-dimethylamino-3-(3-fluorophenyl)pentamethylene)-2-benzoyl-1,3,4,9-tetrahydro-2,9-diazafluorene;
62 1,1-(3-dimethylamino-3-phenylpentamethylene)-2-(cyclohexylcarbonyl)-1,3,4,9-tetrahydro-2,9-diazafluorene;
63 1,1-(3-dimethylamino-3-(3-fluorophenyl)pentamethylene)-2-(phenylacetyl)-1,3,4,9-tetrahydro-2,9-diazafluorene;
64 1,1-(3-dimethylamino-3-(3-fluorophenyl)pentamethylene)-2-(4-methoxybenzoyl)-1,3,4,9-tetrahydro-2,9-diazafluorene;
65 1,1-(3-dimethylamino-3-phenylpentamethylene)-2-(4-trifluoromethylbenzoyl)-1,3,4,9-tetrahydro-2,9-diazafluorene;
66 1,1-(3-dimethylamino-3-(3-fluorophenyl)pentamethylene)-2-(thien-2-ylacetyl)-1,3,4,9-tetrahydro-2,9-diazafluorene;
67 1,1-(3-dimethylamino-3-(3-fluorophenyl)pentamethylene)-2-(phenylacetyl)-1,3,4,9-tetrahydro-2,9-diazafluorene;
68 1,1-(3-dimethylamino-3-(3-fluorophenyl)pentamethylene)-2-butanoyl-1,3,4,9-tetrahydro-2,9-diazafluorene;
69 1,1-(3-dimethylamino-3-benzylpentamethylene)-2-(4-trifluoromethylbenzoyl)-1,3,4,9-tetrahydro-2,9-diazafluorene;
70 1,1-(3-dimethylamino-3-benzylpentamethylene)-2-(3-fluoro-5-trifluoromethylbenzoyl)-1,3,4,9-tetrahydro-2,9-diazafluorene;
71 1,1-(3-dimethylamino-3-(3-fluorophenyl)pentamethylene)-2-(2,3-difluorobenzoyl)-1,3,4,9-tetrahydro-2,9-diazafluorene;
72 1,1-(3-dimethylamino-3-(3-fluorophenyl)pentamethylene)-2-(4-methylbenzoyl)-1,3,4,9-tetrahydro-2,9-diazafluorene, and physiologically acceptable salts thereof.

Furthermore, is has been shown that spirocyclic cyclohexane derivatives in which W denotes $NR^4$ and X denotes O are likewise particularly preferred. Accordingly, in the context of the present invention spirocyclic cyclohexane derivatives in which W denotes $NR^4$ and X denotes O are preferred. It is particularly preferred to use compounds selected from the group consisting of:
1 1,1-(3-dimethylamino-3-phenylpentamethylene)-1,3,4,9-tetrahydropyrano[3,4-b]indole;
3 1,1-(3-dimethylamino-3-phenylpentamethylene)-6-fluoro-1,3,4,9-tetrahydropyrano[3,4-b]indole;
4 1,1-(3-dimethylamino-3-(2-thienyl)pentamethylene)-1,3,4,9-tetrahydropyrano[3,4-b]indole;
5 1,1-(3-dimethylamino-3-phenylpentamethylene)-3-methyl-1,3,4,9-tetrahydropyrano[3,4-b]indole;
6 1,1-(3-dimethylamino-3-phenylpentamethylene)-3,6-dimethyl-1,3,4,9-tetrahydropyrano[3,4-b]indole;
7 1,1-(3-dimethylamino-3-(4-fluorophenyl)pentamethylene)-1,3,4,9-tetrahydropyrano[3,4-b]indole;
12 1,1-(3-dimethylamino-3-phenylpentamethylene)-1,3,4,9-tetrahydro-2-aza-9-oxafluorene;
15 1,1-(3-dimethylamino-3-(3-fluorophenyl)pentamethylene)-1,3,4,9-tetrahydropyrano[3,4-b]indole;
16 1,1-(3-dimethylamino-3-phenylpentamethylene)-6-chloro-3-methyl-1,3,4,9-tetrahydropyrano[3,4-b]indole;
18 1,1-(3-dimethylamino-3-(3-thienyl)pentamethylene)-6-fluoro-1,3,4,9-tetrahydropyrano[3,4-b]indole;
21 1,1-(3-dimethylamino-3-phenylpentamethylene)-3-methyl-1,3,4,9-tetrahydropyrano[3,4-b]indole;
23 1,1-(3-dimethylamino-3-phenylpentamethylene)-3-methyl-6-nitro-1,3,4,9-tetrahydropyrano[3,4-b]indole;
24 1,1-(3-dimethylamino-3-(3-thienyl)pentamethylene)-1,3,4,9-tetrahydropyrano[3,4-b]indole;
29 1,1-(3-dimethylamino-3-(2-thienyl)pentamethylene)-6-fluoro-1,3,4,9-tetrahydropyrano[3,4-b]indole 31   1,1-(3-dimethylamino-3-phenylpentamethylene)-6-fluoro-3-methyl-1,3,4,9-tetrahydropyrano[3,4-b]indole;
32   1,1-(3-dimethylamino-3-phenylpentamethylene)-6-hydroxy-1,3,4,9-tetrahydropyrano[3,4-b]indole;
33 1,1-(3-dimethylamino-3-(3-hydroxyphenyl)pentamethylene)-1,3,4,9-tetrahydropyrano[3,4-b]indole;
35 6,6-(3-dimethylamino-3-phenylpentamethylene)-1,2,3,4,4a,6,7,11c-octahydro-5-oxa-7-aza-benzo[c]fluorine;
36   1,1-(3-dimethylamino-3-phenylpentamethylene)-6-methyl-1,3,4,9-tetrahydropyrano[3,4-b]indole;
41   1,1-(3-dimethylamino-3-phenylpentamethylene)-6-bromo-3-methyl-1,3,4,9-tetrahydropyrano[3,4-b]indole;
42   1,1-(3-dimethylamino-3-phenylpentamethylene)-6-fluoro-1,3,4,9-tetrahydropyrano[3,4-b]indole;
43   1,1-(3-dimethylamino-3-phenylpentamethylene)-6-bromo-1,3,4,9-tetrahydropyrano[3,4-b]indole;
44   1,1-(3-dimethylamino-3-phenylpentamethylene)-6-methoxy-1,3,4,9-tetrahydropyrano[3,4-b]indole;
45   1,1-(3-(1-Pyrrolidyl)-3-phenylpentamethylene)-1,3,4,9-tetrahydropyrano[3,4-b]indole;
46   1,1-(3-dimethylamino-3-phenylpentamethylene)-7,8-dichloro-1,3,4,9-tetrahydropyrano[3,4-b]indole;
47   1,1-(3-dimethylamino-3-phenylpentamethylene)-6-(1-benzyl-pyrazol-4-yl)-1,3,4,9-tetrahydropyrano[3,4-b]indole;
48   1,1-(3-Methylamino-3-(2-thienyl)pentamethylene)-1,3,4,9-tetrahydropyrano[3,4-b]indole;
49   1,1-(3-Methylamino-3-(2-thienyl)pentamethylene)-6-fluoro-1,3,4,9-tetrahydropyrano[3,4-b]indole, and
physiologically acceptable salts thereof.

In particular, it is preferred to use compounds selected from the group consisting of:
1   1,1-(3-dimethylamino-3-phenylpentamethylene)-1,3,4,9-tetrahydropyrano[3,4-b]indole
3   1,1-(3-dimethylamino-3-phenylpentamethylene)-6-fluoro-1,3,4,9-tetrahydropyrano[3,4-b]indole
4   1,1-(3-dimethylamino-3-(2-thienyl)pentamethylene)-1,3,4,9-tetrahydropyrano[3,4-b]indole
5   1,1-(3-dimethylamino-3-phenylpentamethylene)-3-methyl-1,3,4,9-tetrahydropyrano[3,4-b]indole
6 1,1-(3-dimethylamino-3-phenylpentamethylene)-3,6-dimethyl-1,3,4,9-tetrahydropyrano[3,4-b]indole
7   1,1-(3-dimethylamino-3-(4-fluorophenyl)pentamethylene)-1,3,4,9-tetrahydropyrano[3,4-b]indole
12 1,1-(3-dimethylamino-3-phenylpentamethylene)-1,3,4,9-tetrahydro-2-aza-9-oxafluorene
15   1,1-(3-dimethylamino-3-(3-fluorophenyl)pentamethylene)-1,3,4,9-tetrahydropyrano[3,4-b]indole
16   1,1-(3-dimethylamino-3-phenylpentamethylene)-6-chloro-3-methyl-1,3,4,9-tetrahydropyrano[3,4-b]indole
18   1,1-(3-dimethylamino-3-(3-thienyl)pentamethylene)-6-fluoro-1,3,4,9-tetrahydropyrano[3,4-b]indole
21   1,1-(3-dimethylamino-3-phenylpentamethylene)-3-methyl-1,3,4,9-tetrahydropyrano[3,4-b]indole
23   1,1-(3-dimethylamino-3-phenylpentamethylene)-3-methyl-6-nitro-1,3,4,9-tetrahydropyrano[3,4-b]indole
24   1,1-(3-dimethylamino-3-(3-thienyl)pentamethylene)-1,3,4,9-tetrahydropyrano[3,4-b]indole
47   1,1-(3-dimethylamino-3-phenylpentamethylene)-6-(1-benzyl-pyrazol-4-yl)-1,3,4,9-tetrahydropyrano[3,4-b]indole
48   1,1-(3-Methylamino-3-(2-thienyl)pentamethylene)-1,3,4,9-tetrahydropyrano[3,4-b]indole, and
physiologically acceptable salts thereof.

It is most particularly preferred to use compounds selected from the group:
1,1-(3-dimethylamino-3-phenylpentamethylene)-1,3,4,9-tetrahydropyrano[3,4-b]indole;
3 1,1-(3-dimethylamino-3-phenylpentamethylene)-6-fluoro-1,3,4,9-tetrahydropyrano[3,4-b]indole;
4   1,1-(3-dimethylamino-3-(2-thienyl)pentamethylene)-1,3,4,9-tetrahydropyrano[3,4-b]indole, and
physiologically acceptable salts thereof.

Also preferred are compounds selected from the group consisting of:
22 1,1-(3-dimethylamino-3-phenylpentamethylene)-1,3,4,9-tetrahydro-2-thia-9-azafluorene;
27   1,1-(3-dimethylamino-3-phenylpentamethylene)-2-oxo-1,3,4,9-tetrahydro-2-thia-9-azafluorene;
28 1,1-(3-dimethylamino-3-phenylpentamethylene)-1,3,4,9-tetrahydro-2-thia-9-azafluorene;
34 1,1-(3-dimethylamino-3-phenylpentamethylene)-1,3,4,9-tetrahydro-2-thia-9-azafluorene, and
physiologically acceptable salts thereof.

The synthesis of the compounds is described in US 2006/004034 A1 and US 2005/066183 A1. The isolation of the compounds according to the invention by column chromatography with silica gel as stationary phase leads to a separation of the different polar diastereomers. These were characterised on the basis of their running time as "non-polar" diastereomer (shorter running time) and "polar" diastereomer (longer running time). Silica gel 60 (0.040-0.063 mm) from E. Merck, Darmstadt, was used. The thin-layer chromatography investigations were carried out with HPTLC precoated plates from E. Merck, Darmstadt. As solvent, for example methanol/ethyl acetate was used in a ratio of 1:1, 2:1, 3:1 or 4:1, preferably 3:1, or methanol/conc. ammonia solution 99.5:0.5 or methanol/ethyl acetate/conc. ammonia solution in a ratio of 66:33:0.5.

The pharmaceutical compositions of the invention optionally contain, besides at least one compound according to the invention, suitable additives and/or auxiliary substances, including carrier materials, fillers, solvents, diluents, coloring agents and/or binders, and may be administered as liquid medicament forms in the form of injection solutions, drops or ointments, as semi-solid medicament forms in the form of granules, tablets, pellets, patches, capsules, plasters/spray plasters or aerosols. The choice of the auxiliary substances etc. as well as the amounts thereof to be used depend on whether the medicament is to be administered orally, perorally, parenterally, intravenously, intraperitoneally, intradermally, intramuscularly, intranasally, buccally, rectally or topically for example to the skin, mucus membranes or to the eyes. For oral application suitable preparations are in the form of tablets, coated tablets, capsules, granules, drops, ointments and syrups, while for parenteral, topical and inhalative application suitable forms are solutions, suspensions, readily reconstitutable dry preparations, as well as sprays. Spirocyclic cyclohexane derivatives according to the invention in depot form, in dissolved form or in a plaster form, optionally with the addition of agents promoting penetration of the skin, are suitable percutaneous application preparations. Orally or percutaneously usable preparation forms can provide for the delayed release of the compounds according to the invention. The compounds according to the invention can also be employed in parenteral long-term depot forms, such as for example implants or implanted pumps. In principle other active constituents known to the person skilled in the art can be added to the medicaments according to the invention.

The amount of active constituent to be administered to the patient varies depending on the patient's weight, form of application, medical implications and the severity of the illness. Normally 0.00005 to 1 mg/kg, preferably 0.0001 to 0.05 mg/kg of at least one spirocyclic cyclohexane derivative according to the invention is applied.

All the aforementioned forms of the medicaments according to the invention also may contain, in addition to at least one compound according to the invention, a further active constituent, in particular an opioid antagonist, preferably naloxone.

Comparative Investigations

For comparison purposes the standard medication levomethadone, which has no significant ORL1 component, was tested in the withdrawal jumping test. Levomethadone, which is one of the standard therapeutic agents used in substitution therapy, likewise induced withdrawal jumping. Among the compounds described in US 2006/004034 A1 and US 2005/066183 A1 are a number of substances with a slight ORL1 component. Two typical members with a slight ORL1 component (compounds m and n) were likewise tested in the withdrawal jumping test and induced withdrawal jumping. This shows the importance of the ORL1 component as regards the suitability of a substance for substitution therapy within the group of compounds described in US 2006/004034 A1 and US 2005/066183 A1.

The properties that are desired in the standard therapeutic agents and which are to some extent manifested include:
1. High opioid potency
2. Full intrinsic activity
3. Long action duration (active metabolites such as for example in the case of LAAM are even desirable in this indication)
4. Slower action on set, especially with oral administration (less "kick")
5. Lower cardio toxicity Whereas with the known standard substances some of these properties are missing or are insufficiently manifested, with the compounds according to the invention all the required properties were present.

The compounds according to the invention show significantly reduced cardiovascular side effects compared to methadone and LAAM. The cardiovascular side effects are attributed to a delayed cardiac repolarisation (manifested as a QTc extension in the outside ECG), which is caused by the blockade of a special potassium channel (HERG) (Kornick et al. Pain 2003, 105, 499-506). Both methadone and LAAM exhibit interactions with the HERG channel (Jiesheng et al., Eur. J. Pharmacol. 2003, 458, 25-29; Katchman et al., J. Pharmacol. Exp. Ther. 2002, 303, 688-694). In connection with the order issued by Orlaam (LAAM) the FDA gave a warning in 2001 about the cardiovascular effects (JAMA 2001, 285, 2705). In the case of the compounds according to the invention it was shown for example that the cardiovascular side effects are significantly less compared to methadone and LAAM.

EXAMPLES

Within the group of spiro compounds described in US 2006/004034 A1 and US 2005/192333 A1 there are compounds with a higher and lower ORL1 component.

Measurement of the ORL1 Binding

The cyclohexane derivatives of the general formula I were investigated in a receptor binding assay with $^3$H-nociceptin/ orphanin FQ with membranes of recombinant CHO-ORL1 cells. This test system was implemented according to the method proposed by Ardati et al. (Mol. Pharmacol., 51, 1997, pp. 816-824). The concentration of 3H-nociceptin/orphanin FQ in these tests was 0.5 nM. The binding assays were carried out with 20 µg of membrane protein per 200 µl of batch in 50 mM Hepes, pH 7.4, 10 mM $MgCl_2$ and 1 mM EDTA. The binding to the ORL1 receptor was determined using in each case 1 mg WGA-SPA beads (Amersham-Pharmacia, Freiburg), by incubating the batch for one hour at room temperature followed by measurement in a Trilux scintillation counter (Wallac, Finland). The affinity is given in Table 1 as nanomolar $Ki_j$ value in or % inhibition at c=1 µM.

Measurement of the µ-binding

The receptor affinity for the human µ-opiate receptor was determined in a homogeneous batch in mikrotiter plates. For this purpose dilution series of the respective substituted cyclohexyl-1,4-diamine derivatives to be tested were incubated with a receptor membrane preparation (15-40 µg protein per 250 µl incubation batch) of CHO-K1 cells which express the human µ-opiate receptor (RB-HOM receptor membrane preparation obtained from the NEN company, Zaventem, Belgium) in the presence of 1 nmol/l of the radioactive ligand [3H]-naloxone (NET719, NEN company, Zaventem, Belgium) as well as of 1 mg WGA-SPA beads (wheat germ agglutinin SPA Beads from Amersham/Pharmacia, Freiburg, Germany) in a total volume of 250 µl for 90 minutes at room temperature. 50 mmol/l tris-HCl supplemented by 0.05 wt. % of sodium azide and 0.06 wt. % of bovine serum albumin were used as incubation buffer. In order to determine the non-specific binding, 25 µmol/l of naloxone were additionally added. After the end of the 9-minute incubation period the microtiter plates were centrifuged for 20 minutes at 1000 G and the radioactivity was measured in a β-counter (Microbeta-Trilux, PerkinElmer Wallac Company, Freiburg, Germany). The percentage displacement of the radioactive ligand from its binding to the human µ-opiate receptor at a concentration of the test substances of 1 µmol/l was determined and given as the percentage inhibition (% inhibition) of the specific binding. In some cases $IC_{50}$ inhibition concentrations which effect a 50% displacement of the radioactive ligand were calculated on the basis of the percentage displacement by different concentration of the compounds of the general formula I to be tested. Ki values for the test substances were obtained by conversion using the Cheng-Prusoff relationship.

The following table lists by way of example some compounds which, although they bind very well to the µ-opiate receptor, nevertheless have a relatively low ORL1 component:

| Compound | Structure | ORL1/μ ratio calculated as Ki(μ)/Ki(ORL1) (only for measured Ki values) | ORL-1 [1 μM], % inhibition | μ-opiate-receptor [1 μM], % inhibition |
|---|---|---|---|---|
| a | (structure) HCl |  | 1 | 83 |
| b | (structure) Citrate |  | 5 | 89 |
| c | (structure) Citrate |  | 11 | 74 |
| d | (structure) HCl |  | 13 | 83 |

-continued
| Compound | Structure | ORL1/μ ratio calculated as Ki(μ)/Ki(ORL1) (only for measured Ki values) | ORL-1 [1 μM], % inhibition | μ-opiate-receptor [1 μM], % inhibition |
| --- | --- | --- | --- | --- |
| e | 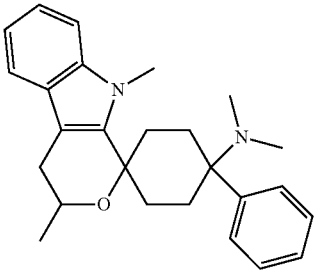<br>Citrate | | 15 | 75 |
| f | 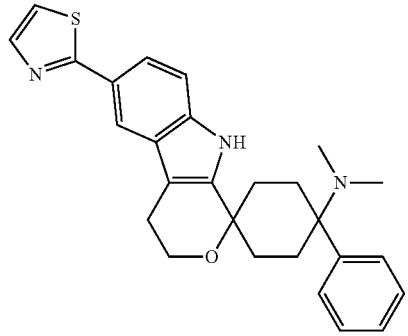<br>Citrate | | 27 | 92 |
| g | 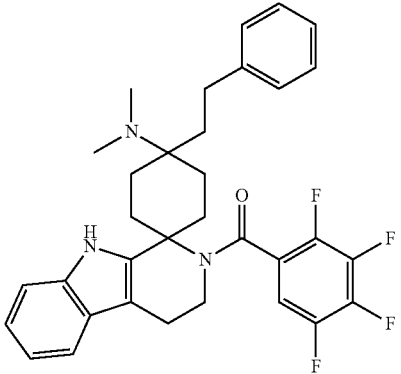 | | 31 | 91 |
| h | 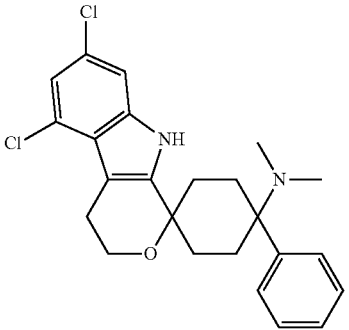 | | 32 | 97 |

-continued

| Compound | Structure | ORL1/μ ratio calculated as Ki(μ)/Ki(ORL1) (only for measured Ki values) | ORL-1 [1 μM], % inhibition | μ-opiate-receptor [1 μM], % inhibition |
|---|---|---|---|---|
| I | 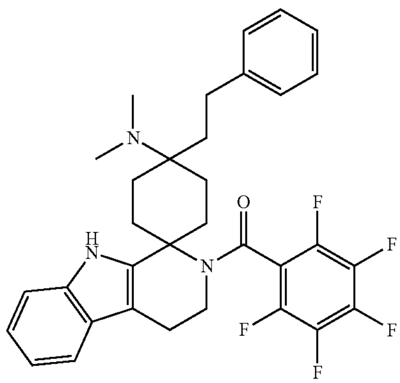 | | 32 | 99 |
| j | Citrate | | 33 | 78 |
| k | 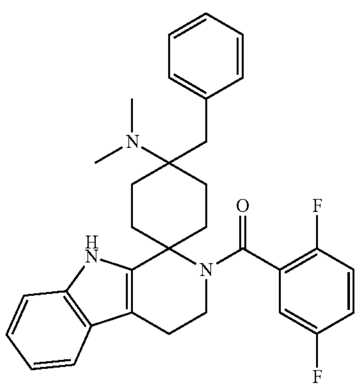 | | 41 | 82 |
| l | Citrate | | 43 | 100 |

| Compound | Structure | ORL1/μ ratio calculated as Ki(μ)/Ki(ORL1) (only for measured Ki values) | ORL-1 [1 μM], % inhibition | μ-opiate-receptor [1 μM], % inhibition |
|---|---|---|---|---|
| m | Citrate | 0.03 | 69 nM ($K_i$) | 2.4 nM ($K_i$) |
| n | Hemicitrate | 0.1 | 14.3 nM ($K_i$) | 1.8 nM ($K_i$) |

As shown by way of example in the compounds m and n, these compounds do not suppress withdrawal jumping.

Compared to the above, the following compounds have an almost balanced ORL1/μ ratio. Ideally, they have a more strongly pronounced ORL1 component. The ORL1:μ ratio is however at least 1:3:

| No. | Compound | Name | Remarks | ORL1/μ Ratio calculated as Ki(μ)/Ki(ORL1) | ORL1 human Ki [μM] | μ Ki [μM] |
|---|---|---|---|---|---|---|
| 1 | | 1,1-(3-dimethylamino-3-phenylpentamethylene)-1,3,4,9-tetrahydropyrano[3,4-b]indole | Hemicitrate Non-polar diastereomer | 2 | 0.0034 | 0.0058 |

-continued

| | | | | | | |
|---|---|---|---|---|---|---|
| 2 | 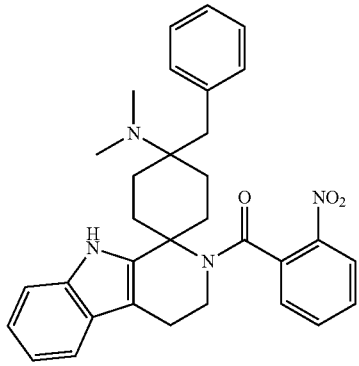 | 1,1-(3-dimethylamino-3-benzylpentamethylene)-2-(2-nitrobenzoyl)-1,3,4,9-tetrahydro-2,9-diazafluorene | | 0.32 | 0.0038 | 0.0012 |
| 3 | 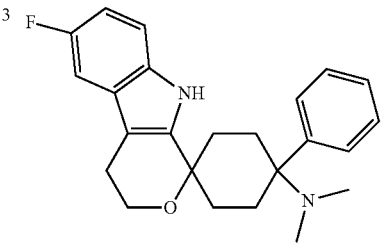 | 1,1-(3-dimethylamino-3-phenylpentamethylene)-6-fluoro-1,3,4,9-tetrahydropyrano[3,4-b]indole | Hemi-citrate Non-polar diastereomer | 2.45 | 0.0026 | 0.006 |
| 4 | 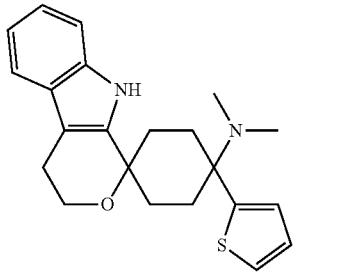 | 1,1-(3-dimethylamino-3-(2-thienyl)pentamethylene)-1,3,4,9-tetrahydropyrano[3,4-b]indole | Hemi-citrate Non-polar diastereomer | 2.07 | 0.0003 | 0.0006 |
| 5 | 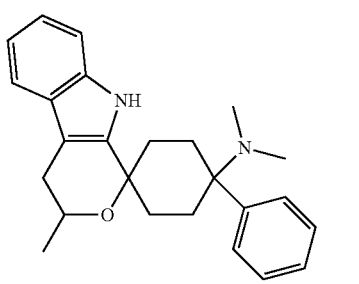 | 1,1-(3-dimethylamino-3-phenylpentamethylene)-3-methyl-1,3,4,9-tetrahydropyrano[3,4-b]indole | Hemi-citrate Non-polar diastereomer | 3.82 | 0.0012 | 0.0047 |
| 6 | 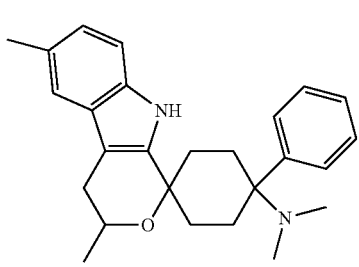 | 1,1-(3-dimethylamino-3-phenylpentamethylene)-3,6-dimethyl-1,3,4,9-tetrahydropyrano[3,4-b]indole | Hemi-citrate One of two diastereomers | 3.18 | 0.0044 | 0.014 |

-continued

| | | | | | | |
|---|---|---|---|---|---|---|
| 7 | | 1,1-(3-dimethylamino-3-(4-fluorophenyl)-pentamethylene)-1,3,4,9-tetrahydro-pyrano[3,4-b]indole | Hemi-citrate One of two dia-stereo-mers | 3.00 | 0.0032 | 0.010 |
| 8 | | 1,1-(3-dimethylamino-3-phenylpentamethyl-ene)-3-hydroxymethyl-1,3,4,9-tetrahydro-2,9-diazafluorene | Di-citrate Dia-stereo-mer mixture | 2.70 | 0.0010 | 0.0027 |
| 9 | | 1,1-(3-dimethylamino-3-phenylpentamethyl-ene)-2-(2,3,4,5,6-pentafluorobenzoyl)-1,3,4,9-tetrahydro-2,9-diazafluorene | | 0.32 | 0.13 | 0.041 |
| 10 | | 1,1-(3-dimethylamino-3-phenylpentamethyl-ene)-2-(methoxy-carbonyl)-1,3,4,9-tetrahydro-2,9-diazafluorene | Citrate Dia-stereo-mer Mixture | 2.67 | 0.0009 | 0.0023 |
| 11 | | 1,1-(3-dimethylamino-3-phenylpentamethyl-ene)-7-fluoro-1,3,4,9-tetrahydro-2,9-diazafluorene | Citrate Polar Dia-stereo-mer | 2.46 | 0.007 | 0.02 |

-continued

| | | | | | | |
|---|---|---|---|---|---|---|
| 12 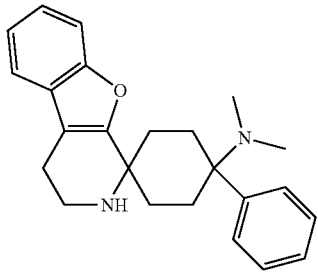 | 1,1-(3-dimethylamino-3-phenylpentamethylene)-1,3,4,9-tetrahydro-2-aza-9-oxafluorene | Citrate Diastereomer mixture | 2.39 | 0.07 | 0.17 |
| 13 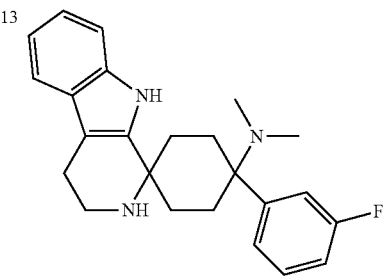 | 1,1-(3-dimethylamino-3-(3-fluorophenyl)-pentamethylene)-1,3,4,9-tetrahydro-2,9-diazafluorene | Diastereomer mixture | 2.22 | 0.0036 | 0.008 |
| 14 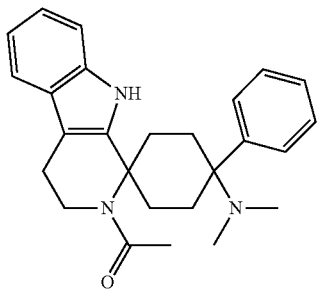 | 1,1-(3-dimethylamino-3-phenylpentamethylene)-2-acetyl-1,3,4,9-tetrahydro-2,9-diazafluorene | hydrochloride Non-polar diastereomer | 1.98 | 0.0029 | 0.006 |
| 15 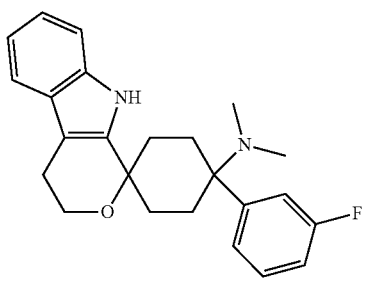 | 1,1-(3-dimethylamino-3-(3-fluorophenyl)-pentamethylene)-1,3,4,9-tetrahydropyrano[3,4-b]indole | Hemi-citrate One of two diastereomers | 1.79 | 0.0012 | 0.0022 |
| 16 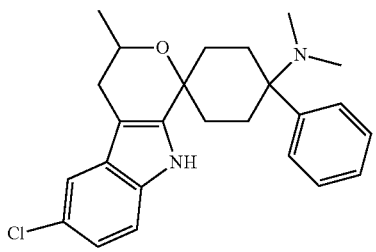 | 1,1-(3-dimethylamino-3-phenylpentamethylene)-6-chloro-3-methyl-1,3,4,9-tetrahydropyrano[3,4-b]indole | Citrate Non-polar diastereomer | 1.77 | 0.06 | 0.11 |

-continued

| | | | | | | |
|---|---|---|---|---|---|---|
| 17 | | 1,1-(3-dimethylamino-3-(2-pyridyl)penta-methylene)-1,3,4,9-tetrahydro-2,9-diazafluorene | Diastereomer mixture | 1.75 | 0.0016 | 0.0028 |
| 18 | | 1,1-(3-dimethylamino-3-(3-thienyl)penta-methylene)-6-fluoro-1,3,4,9-tetrahydro-pyrano[3,4-b]indole | Hemi-citrate Non-polar Diastereomer | 1.62 | 0.0003 | 0.0006 |
| 19 | | 1,1-(3-dimethylamino-3-phenylpentamethyl-ene)-2-acetyl-7-fluoro-1,3,4,9-tetrahydro-2,9-diazafluorene | Citrate Diastereomer mixture | 1.41 | 0.0011 | 0.0016 |
| 20 | | 1,1-(3-dimethylamino-3-phenylpentamethyl-en)-1,3,4,9-tetrahydro-2,9-diazafluorene | Dihydrochloride Diastereomer mixture | 1.38 | 0.0003 | 0.0004 |
| 21 | | 1,1-(3-dimethylamino-3-phenylpentamethyl-ene)-3-methyl-1,3,4,9-tetrahydropyrano[3,4-b]indole | Citrate Diastereomer mixture | 1.38 | 0.04 | 0.06 |

-continued

| | | | | | | |
|---|---|---|---|---|---|---|
| 22 | | 1,1-(3-dimethylamino-3-phenylpentamethyl-en)-1,3,4,9-tetrahydro-2-thia-9-azafluorene | Citrate Diastereomer mixture | 1.33 | 0.02 | 0.02 |
| 23 | | 1,1-(3-dimethylamino-3-phenylpentamethyl-ene)-3-methyl-6-nitro-1,3,4,9-tetrahydro-pyrano[3,4-b]indole | Citrate Polar diastereomer | 1.29 | 0.03 | 0.04 |
| 24 | | 1,1-(3-dimethylamino-3-(3-thienyl)penta-methylene)-1,3,4,9-tetrahydropyrano-[3,4-b]indole | Hemi-citrate Non-polar diastereomer | 1.19 | 0.0006 | 0.0007 |
| 25 | | 1,1-(3-dimethylamino-3-(4-fluorophenyl)-pentamethylene)-1,3,4,9-tetrahydro-2,9-diazafluorene | Diastereomer mixture | 1.12 | 0.0026 | 0.0029 |
| 26 | | 1,1-(3-dimethylamino-3-phenylpentamethyl-ene)-3-methyl-1,3,4,9-tetrahydro-2,9-iazafluorene | Citrate One of two diastereomers | 0.94 | 0.0005 | 0.0005 |

| | | | | | |
|---|---|---|---|---|---|
| 27 | 1,1-(3-dimethylamino-3-phenylpentamethyl-ene)-2-oxo-1,3,4,9-tetrahydro-2-thia-9-azafluorene | Citrate | 0.94 | 0.06 | 0.06 |
| 28 | 1,1-(3-dimethylamino-3-phenylpentamethyl-en)-1,3,4,9-tetrahydro-2-thia-9-azafluorene | Hemi-citrate Non-polar dia-stereo-mer | 0.84 | 0.0037 | 0.0031 |
| 29 | 1,1-(3-dimethylamino-3-(2-thienyl)penta-methylene)-6-fluoro-1,3,4,9-tetrahydro-pyrano[3,4-b]indole | Hemi-citrate Non-polar dia-stereo-mer | 0.82 | 0.0007 | 0.0006 |
| 30 | 1,1-(3-dimethylamino-3-phenylpentamethyl-ene)-3-methyl-1,3,4,9-tetrahydro-2,9-diazafluorene | Di-hydro-chloride Dia-stereo-mer mixture | 0.78 | 0.0006 | 0.0005 |
| 31 | 1,1-(3-dimethylamino-3-phenylpentamethyl-ene)-6-fluoro-3-methyl-1,3,4,9-tetrahydropyrano-[3,4-b]indole | Hemi-citrate One of two dia-stereo-mers | 0.73 | 0.08 | 0.06 |
| 32 | 1,1-(3-dimethylamino-3-phenylpentamethyl-ene)-6-hydroxy-1,3,4,9-tetrahydro-pyrano[3,4-b]indole | Citrate One of two dia-stereo-mers | 0.7 | 0.0016 | 0.0011 |

| | | | | | | |
|---|---|---|---|---|---|---|
| 33 | 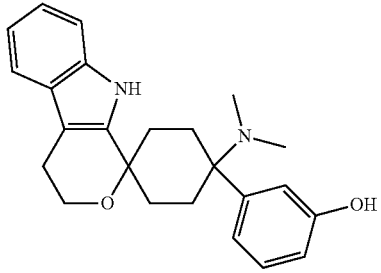 | 1,1-(3-dimethylamino-3-(3-hydroxyphenyl)-pentamethylene)-1,3,4,9-tetrahydro-pyrano[3,4-b]indole | Methyl-sulfonate One of two diastereomers | 0.66 | 0.014 | 0.009 |
| 34 | 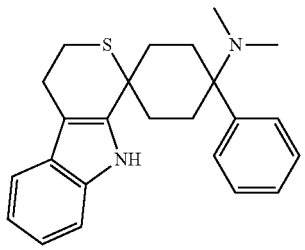 | 1,1-(3-dimethylamino-3-phenylpentamethyl-en)-1,3,4,9-tetrahydro-2-thia-9-azafluorene | Citrate Polar diastereomer | 0.62 | 0.13 | 0.08 |
| 35 | 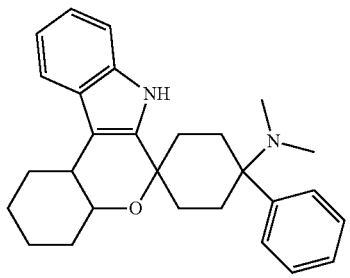 | 6,6-(3-dimethylamino-3-phenylpentamethyl-en)-1,2,3,4,4a,6,7,11c-octahydro-5-oxa-7-aza-benzo[c]fluorine | Citrate Diastereomer mixture | 0.62 | 0.11 | 0.07 |
| 36 | 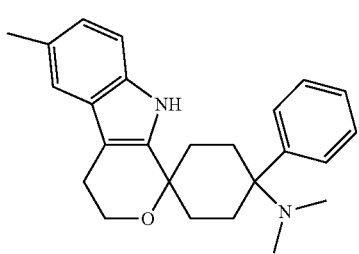 | 1,1-(3-dimethylamino-3-phenylpentamethyl-ene)-6-methyl-1,3,4,9-tetrahydropyrano-[3,4-b]indole | Hemi-citrate One of two diastereomers | 0.60 | 0.0045 | 0.0027 |
| 37 | 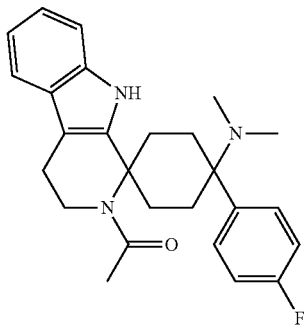 | 1,1-(3-dimethylamino-3-(4-fluorophenyl)-pentamethylene)-2-acetyl-1,3,4,9-tetrahydro-2,9-diazafluorene | Citrate Diastereomer mixture | 0.55 | 0.006 | 0.0033 |
| 38 | 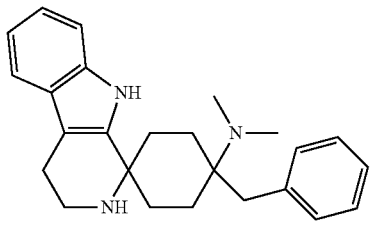 | 1,1-(3-dimethylamino-3-benzylpentamethyl-en)-1,3,4,9-tetrahydro-2,9-diazafluorene | One of two diastereomers | 0.54 | 0.0011 | 0.0006 |

-continued

| | | | | | | |
|---|---|---|---|---|---|---|
| 39 | (structure) | 1,1-(3-dimethylamino-3-phenylpentamethyl-ene)-6-fluoro-1,3,4,9-tetrahydro-2,9-diazafluorene | Di-hydrochloride One of two diastereomers | 0.51 | 0.0014 | 0.0007 |
| 40 | (structure) | 1,1-(3-dimethylamino-3-phenylpentamethyl-ene)-6-methyl-1,3,4,9-tetrahydro-2,9-diazafluorene | Citrate Polar diastereomer | 0.47 | 0.03 | 0.02 |
| 41 | (structure) | 1,1-(3-dimethylamino-3-phenylpentamethyl-ene)-6-bromo-3-methyl-1,3,4,9-tetrahydropyrano-[3,4-b]indole | Hemi-citrate One of two diastereomers | 0.45 | 0.02 | 0.010 |
| 42 | (structure) | 1,1-(3-dimethylamino-3-phenylpentamethyl-ene)-6-fluoro-1,3,4,9-tetrahydropyrano-[3,4-b]indole | Citrate Polar diastereomer | 0.42 | 0.02 | 0.009 |
| 43 | (structure) | 1,1-(3-dimethylamino-3-phenylpentamethyl-ene)-6-bromo-1,3,4,9-tetrahydropyrano-[3,4-b]indole | Hemi-citrate One of two diastereomers | 0.37 | 0.05 | 0.02 |
| 44 | (structure) | 1,1-(3-dimethylamino-3-phenylpentamethyl-ene)-6-methoxy-1,3,4,9-tetrahydro-pyrano[3,4-b]indole | hydrochloride Non-polar diastereomer | 0.34 | 0.006 | 0.0020 |

-continued

| | | | | | | |
|---|---|---|---|---|---|---|
| 45 | 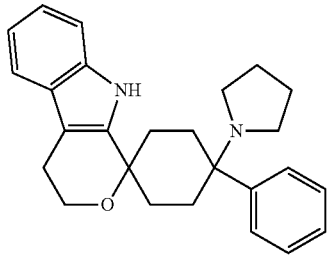 | 1,1-(3-(1-Pyrrolidyl)-3-phenylpentamethylen)-1,3,4,9-tetrahydropyrano[3,4-b]indole | Hemi-citrate Non-polar diastereomer | 0.31 | 0.0035 | 0.0011 |
| 46 | 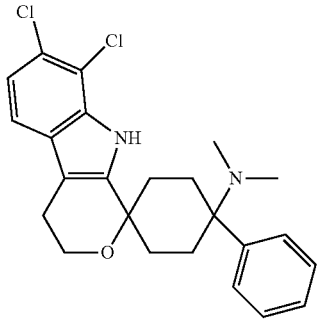 | 1,1-(3-dimethylamino-3-phenylpentamethylene)-7,8-dichloro-1,3,4,9-tetrahydropyrano[3,4-b]indole | Methane sulfonate One of two diastereomers | 0.31 | 0.0045 | 0.0014 |
| 47 | 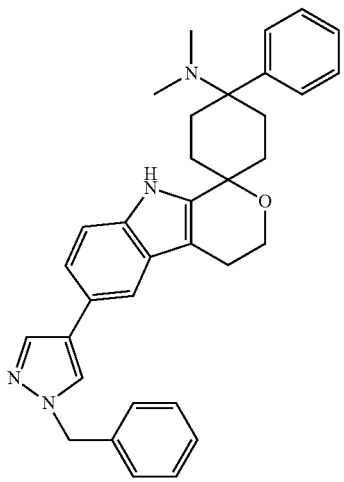 | 1,1-(3-dimethylamino-3-phenylpentamethylene)-6-(1-benzyl-pyrazol-4-yl)-1,3,4,9-tetrahydropyrano-[3,4-b]indole | hydrochloride Non-polar diastereomer | 2.73 | 0.0044 | 0.012 |
| 48 | 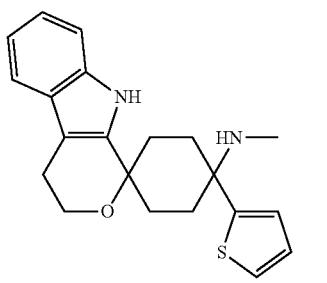 | 1,1-(3-Methylamino-3-(2-thienyl)pentamethylene)-1,3,4,9-tetrahydropyrano[3,4-b]-indole | One of two diastereomers | 6.56 | 0.00032 | 0.0021 |

-continued

| No. | Compound | Name | | | |
|---|---|---|---|---|---|
| 49 | (structure) | 1,1-(3-Methylamino-3-(2-thienyl)pentamethylene)-6-fluoro-1,3,4,9-tetrahydropyrano[3,4-b]indole | Citrate One of two diastereomers | 0.7 | 0.0042 | 0.0028 |

| No. | Compound | Name | ORL1/µ ratio | ORL1, Ki [µM] | µ, Ki [µM] |
|---|---|---|---|---|---|
| 50 | (structure) | 1,1-(3-dimethylamino-3-(3-fluorophenyl)pentamethylene)-2-cinnamoyl-1,3,4,9-tetrahydro-2,9-diazafluorene | 21.43 | 0.0014 | 0.030000 |
| 51 | (structure) | 1,1-(3-dimethylamino-3-(3-fluorophenyl)pentamethylene)-2-(3,3-dimethylbutanoyl)-1,3,4,9-tetrahydro-2,9-diazafluorene | 5.00 | 0.0026 | 0.013000 |
| 52 | (structure) | 1,1-(3-dimethylamino-3-(3-fluorophenyl)pentamethylene)-2-(cyclopentylcarbonyl)-1,3,4,9-tetrahydro-2,9-diazafluorene | 4.78 | 0.0067 | 0.032 |
| 53 | (structure) | 1,1-(3-dimethylamino-3-phenylpentamethylene)-2-(3,3-dimethylbutanoyl)-1,3,4,9-tetrahydro-2,9-diazafluorene | 3.54 | 0.0048 | 0.017 |

| # | Structure | Name | | | |
|---|---|---|---|---|---|
| 54 | 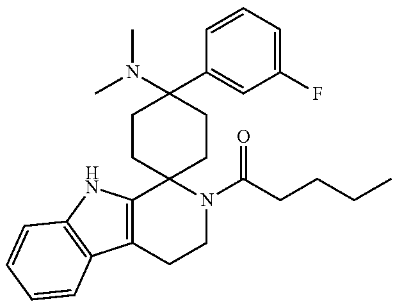 | 1,1-(3-dimethylamino-3-(3-fluorophenyl)pentamethylene)-2-(pentanoyl)-1,3,4,9-tetrahydro-2,9-diazafluorene | 3.42 | 0.0038 | 0.013 |
| 55 | 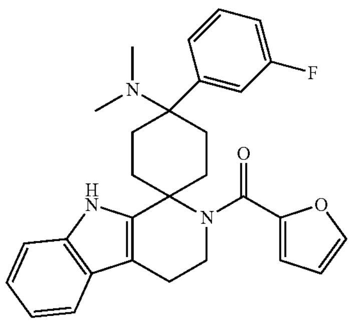 | 1,1-(3-dimethylamino-3-(3-fluorophenyl)pentamethylene)-2-(2-furylcarbonyl)-1,3,4,9-tetrahydro-2,9-diazafluorene | 3.14 | 0.022 | 0.069 |
| 56 | 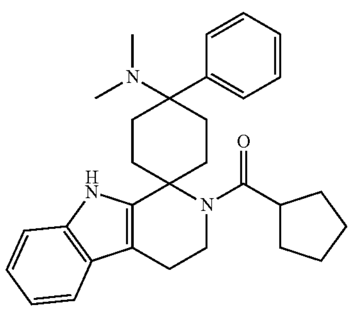 | 1,1-(3-dimethylamino-3-phenylpentamethylene)-2-(2-furylcarbonyl)-1,3,4,9-tetrahydro-2,9-diazafluorene | 2.90 | 0.01 | 0.029 |
| 57 | 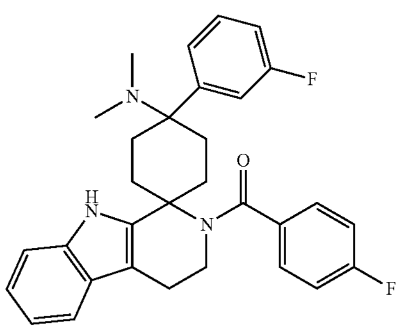 | 1,1-(3-dimethylamino-3-(3-fluorophenyl)pentamethylene)-2-(4-fluorobenzoyl)-1,3,4,9-tetrahydro-2,9-diazafluorene | 2.83 | 0.0046 | 0.013 |
| 58 | 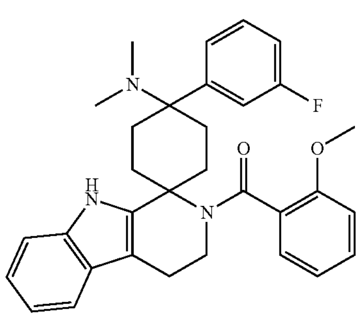 | 1,1-(3-dimethylamino-3-(3-fluorophenyl)pentamethylene)-2-(2-methoxybenzoyl)-1,3,4,9-tetrahydro-2,9-diazafluorene | 2.78 | 0.00097 | 0.0027 |

-continued

| | | | | | |
|---|---|---|---|---|---|
| 59 | 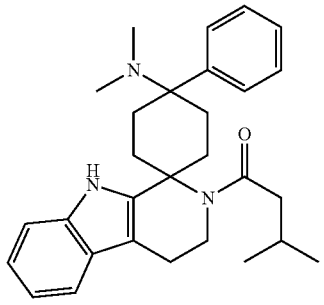 | 1,1-(3-dimethylamino-3-phenylpentamethylene)-2-(3-methylbutanoyl)-1,3,4,9-tetrahydro-2,9-diazafluorene | 2.68 | 0.0041 | 0.011 |
| 60 | 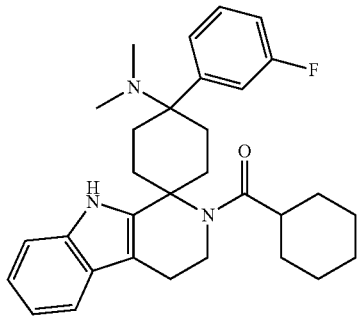 | 1,1-(3-dimethylamino-3-(3-fluorophenyl)pentamethylene)-2-(cyclohexylcarbonyl)-1,3,4,9-tetrahydro-2,9-diazafluorene | 2.60 | 0.025 | 0.065 |
| 61 | 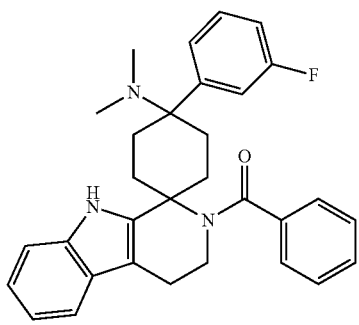 | 1,1-(3-dimethylamino-3-(3-fluorophenyl)pentamethylene)-2-benzoyl-1,3,4,9-tetrahydro-2,9-diazafluorene | 2.50 | 0.0034 | 0.0085 |
| 62 | 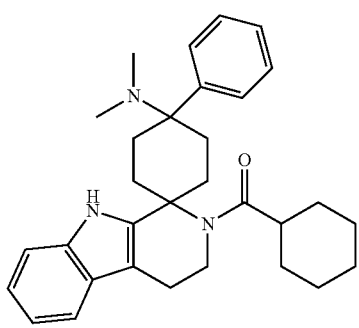 | 1,1-(3-dimethylamino-3-phenylpentamethylene)-2-(cyclohexylcarbonyl)-1,3,4,9-tetrahydro-2,9-diazafluorene | 2.40 | 0.002 | 0.0048 |
| 63 | 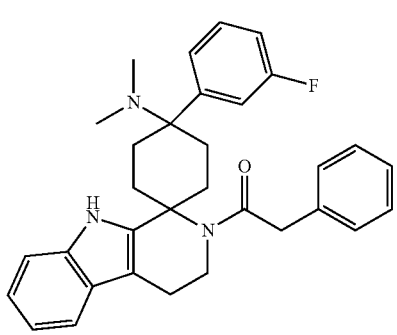 | 1,1-(3-dimethylamino-3-(3-fluorophenyl)pentamethylene)-2-(phenylacetyl)-1,3,4,9-tetrahydro-2,9-diazafluorene | 2.35 | 0.002 | 0.0047 |

-continued

| | | | | | |
|---|---|---|---|---|---|
| 64 | 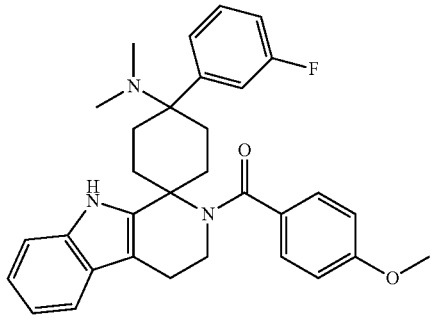 | 1,1-(3-dimethylamino-3-(3-fluorophenyl)pentamethylene)-2-(4-methoxybenzoyl)-1,3,4,9-tetrahydro-2,9-diazafluorene | 2.29 | 0.038 | 0.087 |
| 65 | 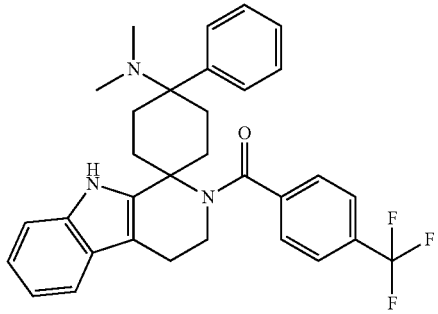 | 1,1-(3-dimethylamino-3-phenylpentamethylene)-2-(4-trifluoromethylbenzoyl)-1,3,4,9-tetrahydro-2,9-diazafluorene | 2.18 | 0.0078 | 0.017 |
| 66 | 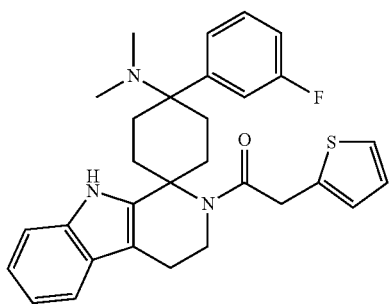 | 1,1-(3-dimethylamino-3-(3-fluorophenyl)pentamethylene)-2-(thien-2-ylacetyl)-1,3,4,9-tetrahydro-2,9-diazafluorene | 2.12 | 0.017 | 0.036 |
| 67 | 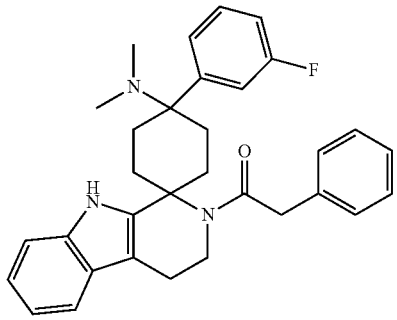 | 1,1-(3-dimethylamino-3-(3-fluorophenyl)pentamethylene)-2-(phenylacetyl)-1,3,4,9-tetrahydro-2,9-diazafluorene | 2.07 | 0.0014 | 0.0029 |
| 68 | 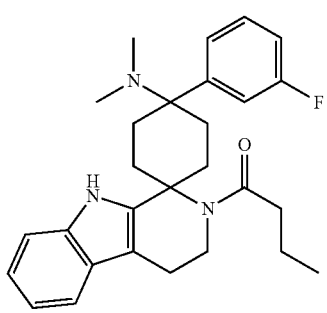 | 1,1-(3-dimethylamino-3-(3-fluorophenyl)pentamethylene)-2-butanoyl-1,3,4,9-tetrahydro-2,9-diazafluorene | 2.00 | 0.0014 | 0.0028 |

| | | | | | |
|---|---|---|---|---|---|
| 69 | | 1,1-(3-dimethylamino-3-benzylpentamethylene)-2-(4-trifluoromethylbenzoyl)-1,3,4,9-tetrahydro-2,9-diazafluorene | 1.91 | 0.011 | 0.021 |
| 70 | | 1,1-(3-dimethylamino-3-benzylpentamethylene)-2-(3-fluoro-5-trifluoromethyl-benzoyl)-1,3,4,9-tetrahydro-2,9-diazafluorene | 1.82 | 0.0077 | 0.014 |
| 71 | | 1,1-(3-dimethylamino-3-(3-fluorophenyl)pentamethylene)-2-(2,3-difluorobenzoyl)-1,3,4,9-tetrahydro-2,9-diazafluorene | 1.79 | 0.0014 | 0.0025 |
| 72 | | 1,1-(3-dimethylamino-3-(3-fluorophenyl)pentamethylene)-2-(4-methylbenzoyl)-1,3,4,9-tetrahydro-2,9-diazafluorene | 1.77 | 0.026 | 0.046 |
| 73 | | 1,1-(3-dimethylamino-3-phenylpentamethylene)-2-(3-phenylpropanoyl)-1,3,4,9-tetrahydro-2,9-diazafluorene | 1.64 | 0.028 | 0.046 |

-continued

| | | | | | |
|---|---|---|---|---|---|
| 74 | 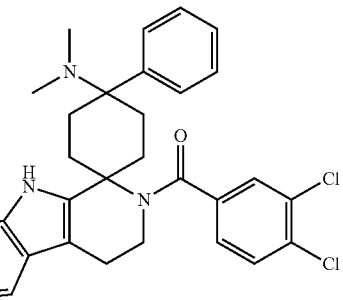 | 1,1-(3-dimethylamino-3-phenylpentamethylene)-2-(3,4-dichlorobenzoyl)-1,3,4,9-tetrahydro-2,9-diazafluorene | 1.64 | 0.014 | 0.023 |
| 75 | 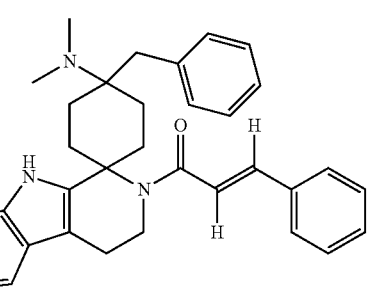 | 1,1-(3-dimethylamino-3-benzylpentamethylene)-2-cinnamoyl-1,3,4,9-tetrahydro-2,9-diazafluorene | 1.54 | 0.024 | 0.037 |
| 76 | 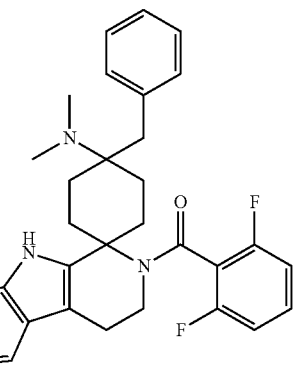 | 1,1-(3-dimethylamino-3-benzylpentamethylene)-2-(2,6-difluorobenzoyl)-1,3,4,9-tetrahydro-2,9-diazafluorene | 1.54 | 0.054 | 0.083 |
| 77 | 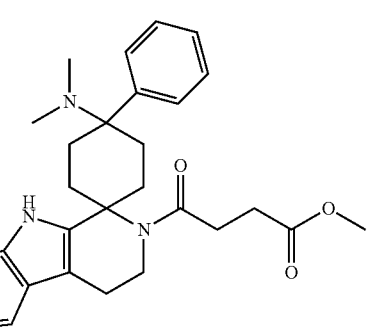 | 1,1-(3-dimethylamino-3-phenylpentamethylene)-2-(3-methoxycarbonylpropanoyl)-1,3,4,9-tetrahydro-2,9-diazafluorene | 1.50 | 0.01 | 0.015 |
| 78 | 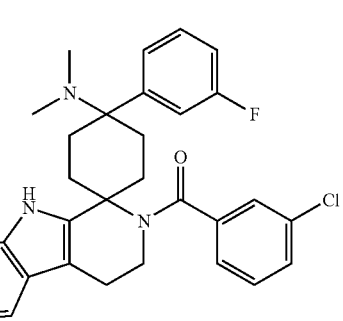 | 1,1-(3-dimethylamino-3-(3-fluorophenyl)pentamethylene)-2-(3-chlorobenzoyl)-1,3,4,9-tetrahydro-2,9-diazafluorene | 1.50 | 0.018 | 0.027 |

-continued

| | | | | | |
|---|---|---|---|---|---|
| 79 | | 1,1-(3-dimethylamino-3-phenylpentamethylene)-2-(3-fluorobenzoyl)-1,3,4,9-tetrahydro-2,9-diazafluorene | 1.50 | 0.0028 | 0.0042 |
| 80 | | 1,1-(3-dimethylamino-3-phenylpentamethylene)-2-(2,6-difluorobenzoyl)-1,3,4,9-tetrahydro-2,9-diazafluorene | 1.50 | 0.01 | 0.015 |
| 81 | | 1,1-(3-dimethylamino-3-(3-fluorophenyl)pentamethylene)-2-(3,4-dichlorobenzoyl)-1,3,4,9-tetrahydro-2,9-diazafluorene | 1.37 | 0.019 | 0.026 |
| 82 | | 1,1-(3-dimethylamino-3-benzylpentamethylene)-2-(2,3,4,5,6-pentafluorobenzoyl)-1,3,4,9-tetrahydro-2,9-diazafluorene | 1.35 | 0.06 | 0.081 |
| 83 | | 1,1-(3-dimethylamino-3-benzylpentamethylene)-2-cyclohexylcarbonyl-1,3,4,9-tetrahydro-2,9-diazafluorene | 1.31 | 0.013 | 0.017 |

| | | | | | |
|---|---|---|---|---|---|
| 84 | 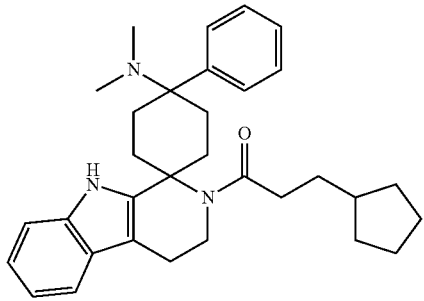 | 1,1-(3-dimethylamino-3-phenylpentamethylene)-2-(3-cyclopentylpropanoyl)-1,3,4,9-tetrahydro-2,9-diazafluorene | 1.29 | 0.0093 | 0.012 |
| 85 | 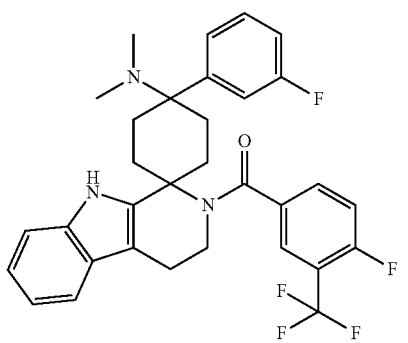 | 1,1-(3-dimethylamino-3-(3-fluorophenyl)pentamethylene)-2-(4-fluoro-3-trifluoromethyl-benzoyl)-1,3,4,9-tetrahydro-2,9-diazafluorene | 1.28 | 0.0071 | 0.0091 |
| 86 | 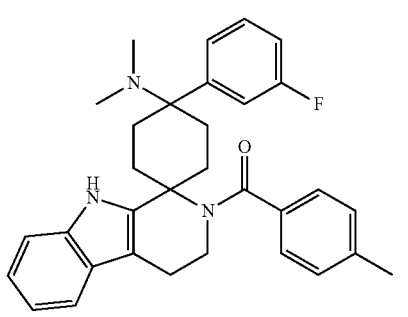 | 1,1-(3-dimethylamino-3-(3-fluorophenyl)pentamethylene)-2-(4-methylbenzoyl)-1,3,4,9-tetrahydro-2,9-diazafluorene | 1.24 | 0.0055 | 0.0068 |
| 87 | 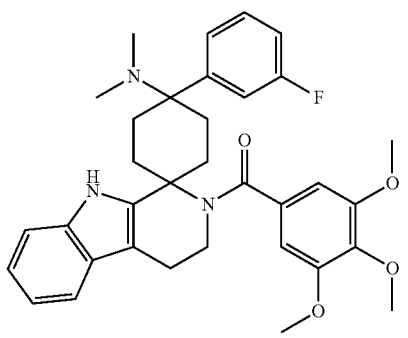 | 1,1-(3-dimethylamino-3-(3-fluorophenyl)pentamethylene)-2-(3,4,5-trimethoxybenzoyl)-1,3,4,9-tetrahydro-2,9-diazafluorene | 1.21 | 0.019 | 0.023 |
| 88 | 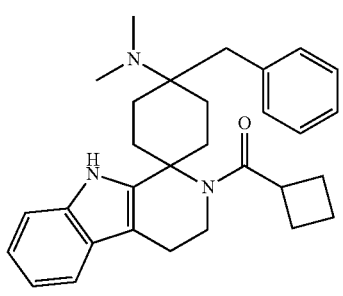 | 1,1-(3-dimethylamino-3-benzylpentamethylene)-2-cyclobutylcarbonyl-1,3,4,9-tetrahydro-2,9-diazafluorene | 1.17 | 0.041 | 0.048 |

| | | | | | |
|---|---|---|---|---|---|
| 89 | (structure) | 1,1-(3-dimethylamino-3-benzylpentamethylene)-2-(2,6-dichlorobenzoyl)-1,3,4,9-tetrahydro-2,9-diazafluorene | 1.14 | 0.029 | 0.033 |
| 90 | (structure) | 1,1-(3-dimethylamino-3-(3-fluorophenyl)pentamethylene)-2-(3-methoxybenzoyl)-1,3,4,9-tetrahydro-2,9-diazafluorene | 1.12 | 0.098 | 0.11 |
| 91 | (structure) | 1,1-(3-dimethylamino-3-phenylpentamethylene)-2-(2-thienylcarbonyl)-1,3,4,9-tetrahydro-2,9-diazafluorene | 1.09 | 0.032 | 0.035 |
| 92 | (structure) | 1,1-(3-dimethylamino-3-(3-fluorophenyl)pentamethylene)-2-propanoyl-1,3,4,9-tetrahydro-2,9-diazafluorene | 1.07 | 0.057 | 0.061 |
| 93 | (structure) | 1,1-(3-dimethylamino-3-(3-fluorophenyl)pentamethylene)-2-(2,4-difluorobenzoyl)-1,3,4,9-tetrahydro-2,9-diazafluorene | 1.06 | 0.016 | 0.017 |

| | | | | | |
|---|---|---|---|---|---|
| 94 | 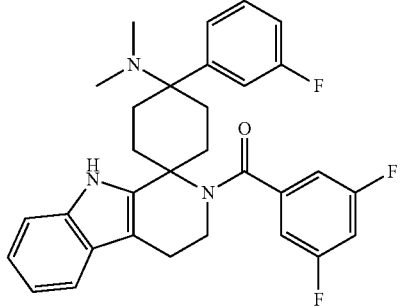 | 1,1-(3-dimethylamino-3-(3-fluorophenyl)pentamethylene)-2-(3,5-difluorobenzoyl)-1,3,4,9-tetrahydro-2,9-diazafluorene | 1.06 | 0.0035 | 0.0037 |
| 95 | 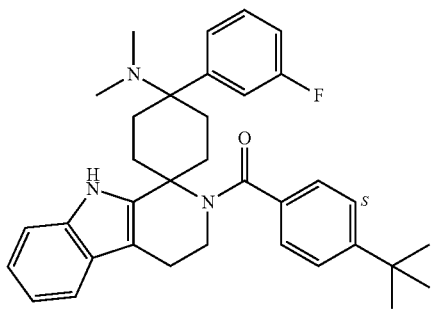 | 1,1-(3-dimethylamino-3-(3-fluorophenyl)pentamethylene)-2-(4-tert.butylbenzoyl)-1,3,4,9-tetrahydro-2,9-diazafluorene | 1.06 | 0.0090 | 0.0095 |
| 96 | 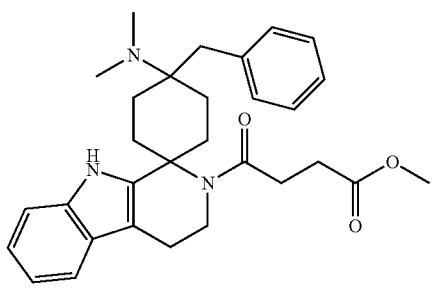 | 1,1-(3-dimethylamino-3-benzylpentamethylene)-2-(3-methoxycarbonylpropanoyl)-1,3,4,9-tetrahydro-2,9-diazafluorene | 1.05 | 0.066 | 0.069 |
| 97 | 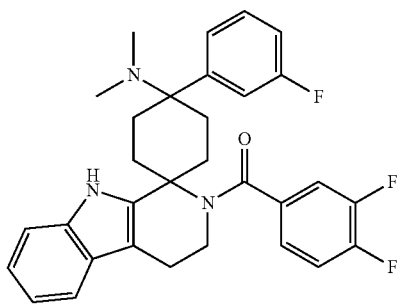 | 1,1-(3-dimethylamino-3-(3-fluorophenyl)pentamethylene)-2-(3,4-difluorobenzoyl)-1,3,4,9-tetrahydro-2,9-diazafluorene | 1.04 | 0.0023 | 0.0024 |
| 98 | 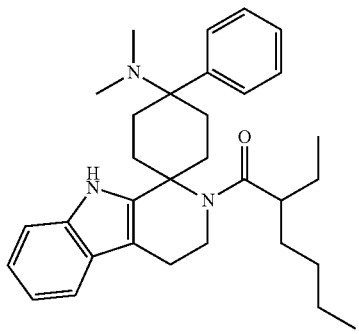 | 1,1-(3-dimethylamino-3-phenylpentamethylene)-2-(2-ethylhexanoyl)-1,3,4,9-tetrahydro-2,9-diazafluorene | 1.04 | 0.047 | 0.049 |

-continued

| | | | | | |
|---|---|---|---|---|---|
| 99 | | 1,1-(3-dimethylamino-3-fluorophenyl)pentamethylene)-2-(2-methylbenzoyl)-1,3,4,9-tetrahydro-2,9-diazafluorene | 1.02 | 0.0092 | 0.0094 |
| 100 | | 1,1-(3-dimethylamino-3-phenylpentamethylene)-2-(3-phenylpropanoyl)-1,3,4,9-tetrahydro-2,9-diazafluorene | 1.00 | 0.04 | 0.04 |
| 101 | | 1,1-(3-dimethylamino-3-fluorophenyl)pentamethylene)-2-(3-fluoro-5-trifluoromethylbenzoyl)-1,3,4,9-tetrahydro-2,9-diazafluorene | 1.00 | 0.0033 | 0.0033 |
| 102 | | 1,1-(3-dimethylamino-3-phenylpentamethylene)-2-(4-fluoro-3-trifluoromethylbenzoyl)-1,3,4,9-tetrahydro-2,9-diazafluorene | 1.00 | 0.036 | 0.036 |
| 103 | | 1,1-(3-dimethylamino-3-fluorophenyl)pentamethylene)-2-(4-nitrobenzoyl)-1,3,4,9-tetrahydro-2,9-diazafluorene | 0.97 | 0.0064 | 0.0062 |

-continued

| | | | | | |
|---|---|---|---|---|---|
| 104 | | 1,1-(3-dimethylamino-3-phenylpentamethylene)-2-(3,5-difluorobenzoyl)-1,3,4,9-tetrahydro-2,9-diazafluorene | 0.95 | 0.002 | 0.0019 |
| 105 | | 1,1-(3-dimethylamino-3-benzylpentamethylene)-2-(2-trifluoromethylbenzoyl)-1,3,4,9-tetrahydro-2,9-diazafluorene | 0.95 | 0.019 | 0.018 |
| 106 | | 1,1-(3-dimethylamino-3-(3-fluorophenyl)pentamethylene)-2-(3,4-difluorobenzoyl)-1,3,4,9-tetrahydro-2,9-diazafluorene | 0.94 | 0.0035 | 0.0033 |
| 107 | | 1,1-(3-dimethylamino-3-phenylpentamethylene)-2-(4-chlorobenzoyl)-1,3,4,9-tetrahydro-2,9-diazafluorene | 0.91 | 0.011 | 0.010 |
| 108 | | 1,1-(3-dimethylamino-3-(3-fluorophenyl)pentamethylene)-2-(3-methylbenzoyl)-1,3,4,9-tetrahydro-2,9-diazafluorene | 0.91 | 0.011 | 0.010 |

-continued

| | | | | | |
|---|---|---|---|---|---|
| 109 | 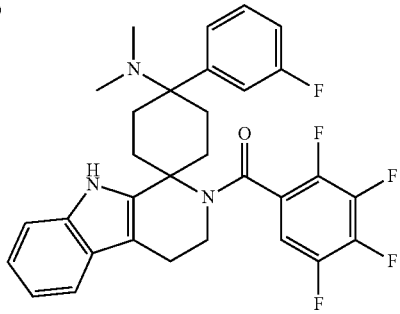 | 1,1-(3-dimethylamino-3-(3-fluorophenyl)pentamethylene)-2-(2,3,4,5-tetrafluorobenzoyl)-1,3,4,9-tetrahydro-2,9-diazafluorene | 0.90 | 0.002 | 0.0018 |
| 110 | 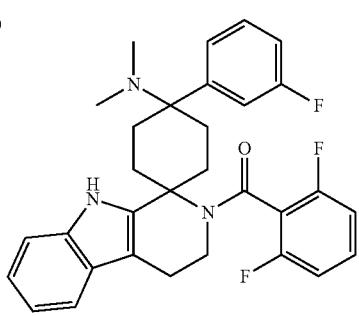 | 1,1-(3-dimethylamino-3-(3-fluorophenyl)pentamethylene)-2-(2,6-difluorobenzoyl)-1,3,4,9-tetrahydro-2,9-diazafluorene | 0.88 | 0.0089 | 0.0078 |
| 111 | 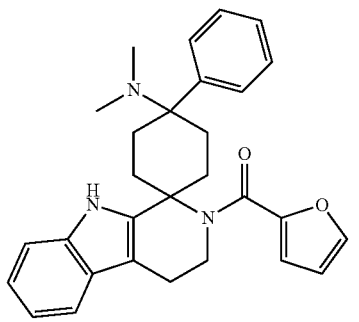 | 1,1-(3-dimethylamino-3-phenylpentamethylene)-2-(2-furylcarbonyl)-1,3,4,9-tetrahydro-2,9-diazafluorene | 0.87 | 0.039 | 0.034 |
| 112 | 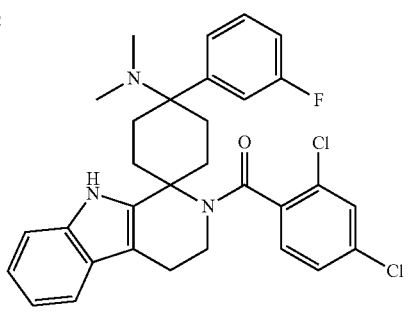 | 1,1-(3-dimethylamino-3-(3-fluorophenyl)pentamethylene)-2-(2,4-dichlorobenzoyl)-1,3,4,9-tetrahydro-2,9-diazafluorene | 0.86 | 0.022 | 0.019 |
| 113 | 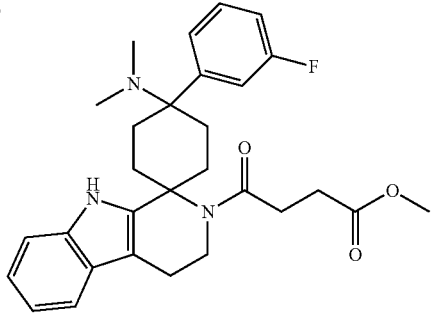 | 1,1-(3-dimethylamino-3-(3-fluorophenyl)pentamethylene)-2-(3-methoxycarbonyl-propanoyl)-1,3,4,9-tetrahydro-2,9-diazafluorene | 0.86 | 0.029 | 0.025 |

| | | | | |
|---|---|---|---|---|
| 114 | 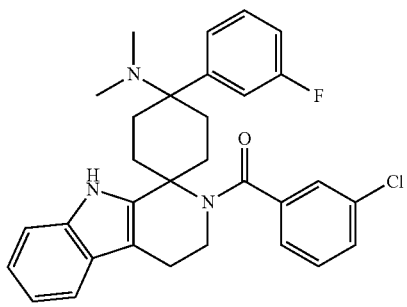 | 1,1-(3-dimethylamino-3-(3-fluorophenyl)pentamethylene)-2-(3-chlorobenzoyl)-1,3,4,9-tetrahydro-2,9-diazafluorene | 0.83 | 0.0075 | 0.0062 |
| 115 | 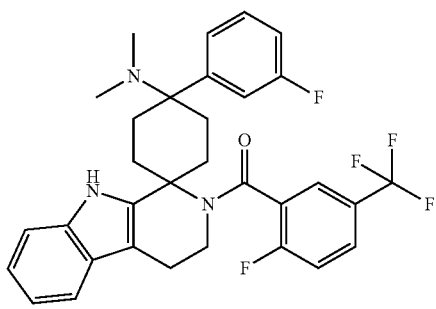 | 1,1-(3-dimethylamino-3-(3-fluorophenyl)pentamethylene)-2-(2-fluoro-5-trifluoromethyl-benzoyl)-1,3,4,9-tetrahydro-2,9-diazafluorene | 0.80 | 0.11 | 0.088 |
| 116 | 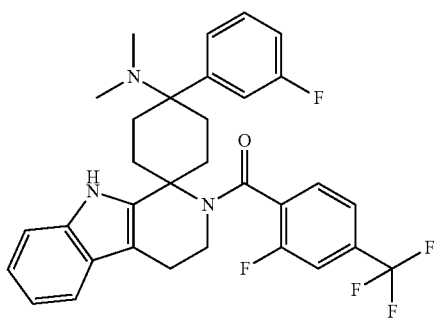 | 1,1-(3-dimethylamino-3-(3-fluorophenyl)pentamethylene)-2-(2-fluoro-4-trifluoro-methylbenzoyl)-1,3,4,9-tetrahydro-2,9-diazafluorene | 0.80 | 0.0044 | 0.0035 |
| 117 | 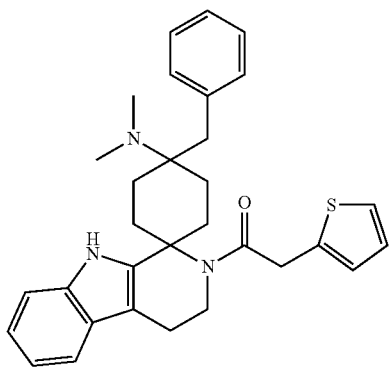 | 1,1-(3-dimethylamino-3-benzylpentamethylene)-2-(2-thienylacetyl)-1,3,4,9-tetrahydro-2,9-diazafluorene | 0.79 | 0.014 | 0.011 |

-continued

| | | | | | |
|---|---|---|---|---|---|
| 118 | 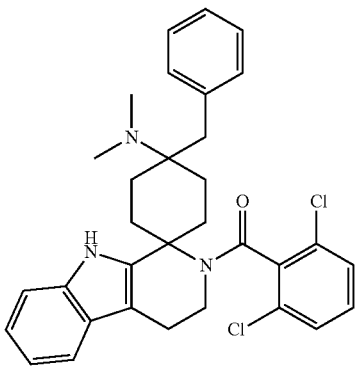 | 1,1-(3-dimethylamino-3-benzylpentamethylene)-2-(2,6-dichlorobenzoyl)-1,3,4,9-tetrahydro-2,9-diazafluorene | 0.78 | 0.093 | 0.073 |
| 119 | 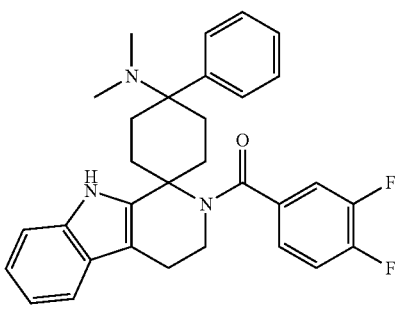 | 1,1-(3-dimethylamino-3-phenylpentamethylene)-2-(3,4-difluorobenzoyl)-1,3,4,9-tetrahydro-2,9-diazafluorene | 0.76 | 0.0025 | 0.0019 |
| 120 | 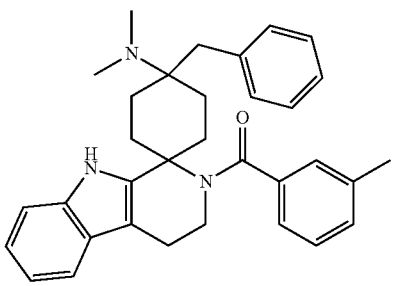 | 1,1-(3-dimethylamino-3-benzylpentamethylene)-2-(3-methylbenzoyl)-1,3,4,9-tetrahydro-2,9-diazafluorene | 0.75 | 0.016 | 0.012 |
| 121 | 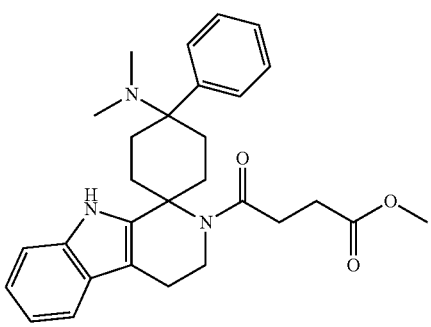 | 1,1-(3-dimethylamino-3-phenylpentamethylene)-2-(3-methoxycarbonylpropanoyl)-1,3,4,9-tetrahydro-2,9-diazafluorene | 0.71 | 0.021 | 0.015 |
| 122 | 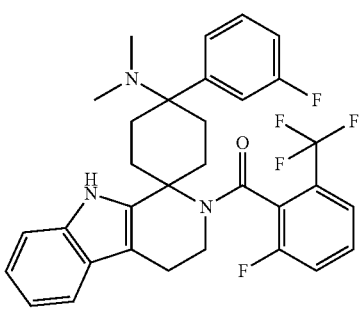 | 1,1-(3-dimethylamino-3-(3-fluorophenyl)pentamethylene)-2-(2-fluoro-6-trifluoromethyl-benzoyl)-1,3,4,9-tetrahydro-2,9-diazafluorene | 0.67 | 0.0054 | 0.0036 |

-continued

| | | | | | |
|---|---|---|---|---|---|
| 123 | 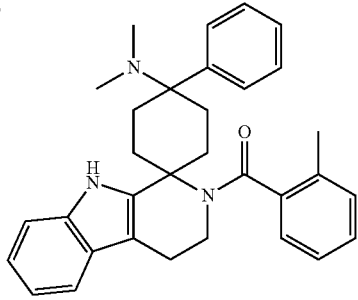 | 1,1-(3-dimethylamino-3-phenylpentamethylene)-2-(2-methylbenzoyl)-1,3,4,9-tetrahydro-2,9-diazafluorene | 0.65 | 0.031 | 0.020 |
| 124 | 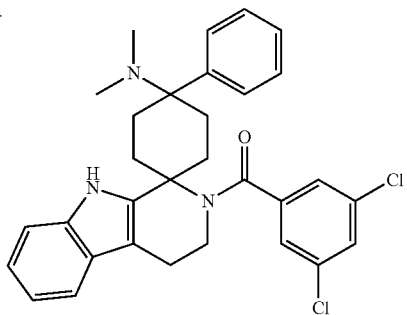 | 1,1-(3-dimethylamino-3-phenylpentamethylene)-2-(3,5-dichlorobenzoyl)-1,3,4,9-tetrahydro-2,9-diazafluorene | 0.64 | 0.0550 | 0.035 |
| 125 | 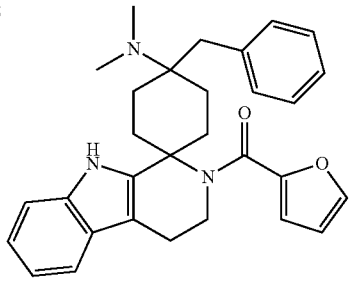 | 1,1-(3-dimethylamino-3-benzylpentamethylene)-2-(2-furylcarbonyl)-1,3,4,9-tetrahydro-2,9-diazafluorene | 0.63 | 0.0054 | 0.0034 |
| 126 | 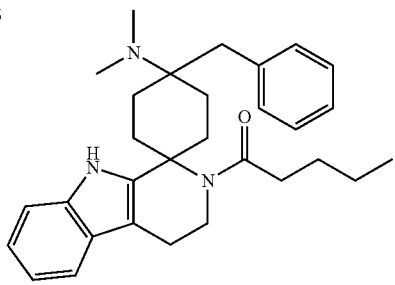 | 1,1-(3-dimethylamino-3-benzylpentamethylene)-2-(pentanoyl)-1,3,4,9-tetrahydro-2,9-diazafluorene | 0.63 | 0.0043 | 0.0027 |
| 127 | 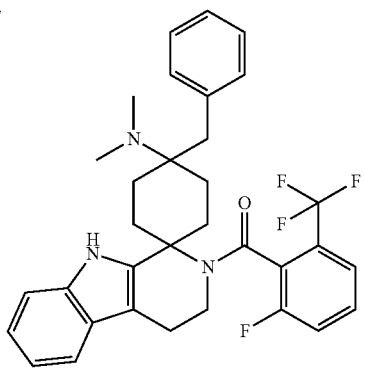 | 1,1-(3-dimethylamino-3-benzylpentamethylene)-2-(6-fluoro-2-trifluoromethyl-benzoyl)-1,3,4,9-tetrahydro-2,9-diazafluorene | 0.62 | 0.055 | 0.034 |

| | | | | | |
|---|---|---|---|---|---|
| 128 | | 1,1-(3-dimethylamino-3-(3-fluorophenyl)pentamethylene)-2-(3-methoxybenzoyl)-1,3,4,9-tetrahydro-2,9-diazafluorene | 0.57 | 0.028 | 0.016 |
| 129 | | 1,1-(3-dimethylamino-3-benzylpentamethylene)-2-(4-tert.butylbenzoyl)-1,3,4,9-tetrahydro-2,9-diazafluorene | 0.54 | 0.11 | 0.059 |
| 130 | | 1,1-(3-dimethylamino-3-benzylpentamethylene)-2-(phenylacetyl)-1,3,4,9-tetrahydro-2,9-diazafluorene | 0.54 | 0.0099 | 0.0053 |
| 131 | | 1,1-(3-dimethylamino-3-(3-fluorophenyl)pentamethylene)-2-(3,5-dichlorobenzoyl)-1,3,4,9-tetrahydro-2,9-diazafluorene | 0.53 | 0.030 | 0.016 |
| 132 | | 1,1-(3-dimethylamino-3-benzylpentamethylene)-2-(2,3,4,5,6-pentafluorobenzoyl)-1,3,4,9-tetrahydro-2,9-diazafluorene | 0.52 | 0.075 | 0.039 |

-continued

| | | | | | |
|---|---|---|---|---|---|
| 133 | | 1,1-(3-dimethylamino-3-benzylpentamethylene)-2-(3-nitrobenzoyl)-1,3,4,9-tetrahydro-2,9-diazafluorene | 0.52 | 0.017 | 0.0088 |
| 134 | | 1,1-(3-dimethylamino-3-phenylpentamethylene)-2-(3-nitrobenzoyl)-1,3,4,9-tetrahydro-2,9-diazafluorene | 0.51 | 0.069 | 0.035 |
| 135 | | 1,1-(3-dimethylamino-3-benzylpentamethylene)-2-(2,3,4,5-tetrafluorobenzoyl)-1,3,4,9-tetrahydro-2,9-diazafluorene | 0.50 | 0.030 | 0.015 |
| 136 | | 1,1-(3-dimethylamino-3-phenylpentamethylene)-2-(2-thienylacetyl)-1,3,4,9-tetrahydro-2,9-diazafluorene | 0.48 | 0.0069 | 0.0033 |
| 137 | | 1,1-(3-dimethylamino-3-phenylpentamethylene)-2-(2-fluoro-4-trifluoromethylbenzoyl)-1,3,4,9-tetrahydro-2,9-diazafluorene | 0.48 | 0.065 | 0.031 |

| | | | | | |
|---|---|---|---|---|---|
| 138 | 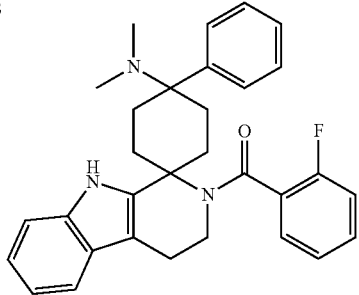 | 1,1-(3-dimethylamino-3-phenylpentamethylene)-2-(2-fluorobenzoyl)-1,3,4,9-tetrahydro-2,9-diazafluorene | 0.47 | 0.018 | 0.0084 |
| 139 | 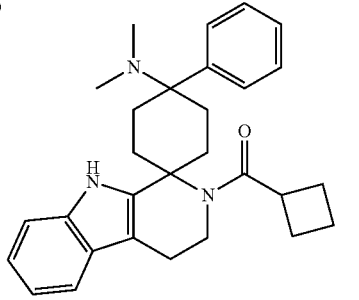 | 1,1-(3-dimethylamino-3-phenylpentamethylene)-2-(cyclobutylcarbonyl)-1,3,4,9-tetrahydro-2,9-diazafluorene | 0.45 | 0.075 | 0.034 |
| 140 | 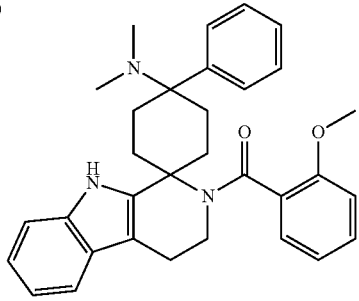 | 1,1-(3-dimethylamino-3-phenylpentamethylene)-2-(2-methoxybenzoyl)-1,3,4,9-tetrahydro-2,9-diazafluorene | 0.43 | 0.046 | 0.020 |
| 141 | 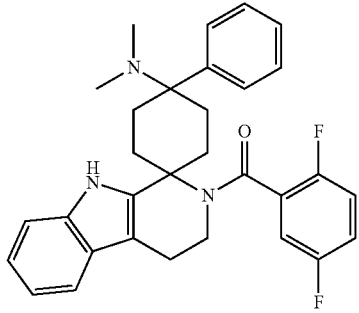 | 1,1-(3-dimethylamino-3-phenylpentamethylene)-2-(2,5-difluorobenzoyl)-1,3,4,9-tetrahydro-2,9-diazafluorene | 0.42 | 0.0045 | 0.0019 |
| 142 | 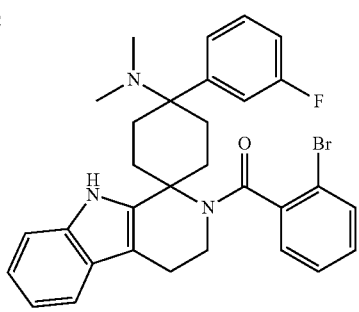 | 1,1-(3-dimethylamino-3-(3-fluorophenyl)pentamethylene)-2-(2-bromobenzoyl)-1,3,4,9-tetrahydro-2,9-diazafluorene | 0.41 | 0.046 | 0.019 |

| | | | | | |
|---|---|---|---|---|---|
| 143 | | 1,1-(3-dimethylamino-3-phenylpentamethylene)-2-(3-fluoro-5-trifluoromethyl-benzoyl)-1,3,4,9-tetrahydro-2,9-diazafluorene | 0.41 | 0.037 | 0.015 |
| 144 | | 1,1-(3-dimethylamino-3-phenylpentamethylene)-2-(2-fluoro-5-trifluoromethyl-benzoyl)-1,3,4,9-tetrahydro-2,9-diazafluorene | 0.39 | 0.049 | 0.019 |
| 145 | | 1,1-(3-dimethylamino-3-phenylpentamethylene)-2-(2,3-difluorobenzoyl)-1,3,4,9-tetrahydro-2,9-diazafluorene | 0.33 | 0.029 | 0.0096 |

Jumping Test in Mice: Experiment to Determine the Systemic Dependency (Saelens J K, Arch Int Pharmacodyn 190: 213-218, 1971)

The test substances were applied intraperitoneally a total of seven times over two days. Five applications were made on the first day at 9:00, 10:00, 11:00, 13:00 and 15:00 hours, and on the second day at 9:00 and 11:00 hours. The first three applications were made in increasing dosages (dosage scheme), the further applications being at the dosage of the third application. The withdrawal symptoms were triggered with 30 mg/kg naloxone (i.p.) two hours after the last substance application. Immediately following this the animals were placed individually in transparent observation cages (height 40 cm, diameter 15 cm) and the jumping reactions were counted over 15 minutes in 5-minute periods in each case. Morphine was administered in a dosage as comparison/standard. The withdrawal symptoms were quantified by counting the number of jumps over 0 to 10 minutes after application of naloxone. The number of animals per group exhibiting more than 10 jumps/10 minutes was determined and recorded as "% positive animals". The average jumping frequency in the group was also calculated. Twelve animals were used per group.

BRIEF DESCRIPTION OF THE DRAWINGS

Results of the jumping tests are shown in the accompanying Figures in which:

FIG. 1 is a graph of the mice jumping test results for levomethadone;

FIG. 2 is a graph of the jumping test results for compound m;

FIG. 3 is a graph of the jumping test results for compound n;

FIG. 4 is a graph of the jumping test results according to Example 1;

FIG. 5 is a graph of the jumping test results according to Example 3, and

FIG. 6 is a graph of the jumping test results according to Example 4.

Investigations of Cardiovascular Effects

ECG Method Description, Conscious Dogs:

Effects of the substances on the heart rate and electrocardiograph parameters were investigated on conscious Beagle dogs. The electrocardiogram measurement was carried out as a bipolar limb lead according to Einthoven (lead II). For this purpose the Beagle dogs were placed in a special hammock-like holder (Animal sling, Havard Instruments, ZAK, Marktheidenfeld, Germany) and loosely secured. A measurement electrode was applied to each of the left and right front limbs, and a reference electrode was also applied to the rear limb. All electrodes were plate electrodes, which were fixed to the shaved skin by rubber collars. The plate electrodes were connected to a ECG pre-amplifier and the signals were continuously digitised by means of a computer-controlled data receiving and archiving system (PO-NE-MAH, Gould-Instrument Systems, USA) (digitising frequency: 2 kHz). The mean values of the following parameters were determined from 10 successive ECG intervals per measurement time: RR interval, PR interval, QRS interval and QT interval. The frequency correction of the QT interval was made according to the correction formula of Van de Water et al. (1989).

Each of the test substances was administered as an i.v. short infusion (15 minutes) via the V. cephalica antibrachii. To quantify effects of substances, the changes in the ECG parameters over a period of 60 minutes after administration of the substance were recorded relative to the base value before administration of the substance. The statistical evaluation was carried out by means of variance analysis (ANOVA) compared to synchronous vehicle control measurements. (Van de Water A, Verheyen J, Xhonneux R, Reneman R S. An improved method to correct the QT interval of the electrocardiogram for changes in heart rate. J Pharmacol Methods. 1989 November; 22(3):207-17).

Patch-clamp, hERG Current

Method description in: Bischoff U, Schmidt C, Netzer R, Pongs O. Effects of fluoroquinolones on HERG currents. Eur J. Pharmacol. 2000; 406(3):341-3.

Blood Pressure, Conscious Rats

Method description in: Weeks J R, Compton L D. The cardiovascular pharmacology of prostacyclin (PGI2) in the rat. Prostaglandins 1979; 17(4):501-13.

TABLE A

Summary of the cardiovascular effects of Example 1:

| Model | Dose | Observation |
|---|---|---|
| Patch clamp, hERG current | | $IC_{50} \gg 10$ µM (10 µM: 29 ± 7% inhibition) |
| Blood pressure, heart rate, conscious rat | Up to 14.7 µg/kg i.v.** | No effect |
| ECG, conscious dog | 10 µg/kg i.v. | Significant Bradycardia (heart rate: −40%) Non-significant extension of the QTc [van der Water] Slight (<10%) significant increase in the QRS time No effect on the PRinterval |

**Tail flick, rat: $EC_{50}$ = 1.44 µg/kg i.v.

For comparison: the $IC_{50}$ value for LAAM is 2 µm (interactions of LAAM/HERG channel, see Jiesheng et al., Eur. J. Pharmacol. 2003, 458, 25-29), the $IC_{50}$ value for methadone is 9.8 µM (see Katchman et al., J. Pharmacol. Exp. Ther. 2002, 303, 688-694).

In conscious rats, no cardiovascular effects are observed with an administration of up to 1 order of magnitude greater than the $EC_{50}$ value in the tail flick test in rats of Example 1.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound corresponding to the formula:

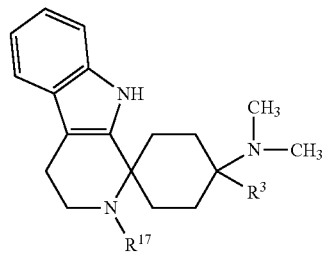

wherein:
$R^3$ denotes phenyl unsubstituted or singly or multiply substituted with F or Cl; and
$R^{17}$ denotes $COR^{12}$, wherein:
  $R^{12}$ denotes:
    branched or unbranched, saturated or unsaturated $C_{1-7}$ alkyl substituted with phenyl, thienyl, $C_{3-6}$-cycloalkyl or $COOC_{1-4}$-alkyl;
    $C_{4-6}$-cycloalkyl;
    furyl;
    thienyl; or
    phenyl, which may be unsubstituted or substituted with 1 to 5 substituents independently selected from the group consisting of F, Cl, Br, —$CF_3$, —$OCH_3$, —$NO_2$, and straight chain or branched $C_{1-4}$ alkyl;
or a physiologically acceptable salt thereof.

2. A compound according to claim 1, wherein $R^3$ denotes a phenyl, 3-fluorophenyl or 4-fluorophenyl group.

3. A compound according to claim 1, wherein $R^{17}$ denotes $COR^{12}$, and $R^{12}$ denotes phenyl, which may be unsubstituted or substituted with 1 to 5 substituents independently selected from the group consisting of F, Cl, Br, —$CF_3$, —$OCH_3$, straight chain or branched $C_{1-4}$ alkyl, and nitro.

4. A compound according to claim 3, wherein $R^{17}$ denotes a benzoyl, 2-bromobenzoyl, 2-fluorobenzoyl, 2-methylbenzoyl, 2-methoxybenzoyl, 3-chlorobenzoyl, 3-fluorobenzoyl, 3-methylbenzoyl, 3-methoxybenzoyl, 3-nitrobenzoyl, 4-chlorobenzoyl, 4-fluorobenzoyl, 4-methylbenzoyl, 4-methoxybenzoyl, 4-nitrobenzoyl, 4-tert.butylbenzoyl, 4-trifluoromethylbenzoyl, 2,3-difluorobenzoyl, 2,4-dichlorobenzoyl, 2,4-difluorobenzoyl, 2-fluoro-4-trifluoromethylbenzoyl, 2,5-difluorobenzoyl, 2-fluoro-5-trifluoromethylbenzoyl, 2,6-difluorobenzoyl, 2-fluoro-6-trifluoromethylbenzoyl, 3,4-dichlorobenzoyl, 3,4-difluorobenzoyl, 3-trifluoromethyl-4-fluorobenzoyl, 3,5-dichlorobenzoyl, 3,5-difluorobenzoyl, 3-fluoro-5-trifluoromethylbenzoyl, 3,4,5-trimethoxybenzoyl, 2,3,4,5-tetrafluorobenzoyl, or 2,3,4,5,6-pentafluorobenzoyl group.

5. A compound according to claim 1, wherein $R^{17}$ denotes a $COR^{12}$ group, and $R^{12}$ denotes a $C_{4-6}$-cycloalkyl, furyl, or thienyl group.

6. A compound according to claim 5, wherein $R^{17}$ denotes a cyclobutylcarbonyl, cyclopentylcarbonyl, cyclohexylcarbonyl, 2-furylcarbonyl, or 2-thienylcarbonyl group.

7. A compound according to claim 1, wherein $R^{17}$ denotes $COR^{12}$, wherein $R^{12}$ denotes a branched or unbranched, saturated or unsaturated $C_{1-7}$-alkyl group unsubstituted or substituted with phenyl, thienyl, $C_{3-6}$-cycloalkyl or $COOC_{1-4}$-alkyl.

8. A compound according to claim 7, wherein $R^{17}$ denotes a phenylacetyl, 2-thienylacetyl, cinnamoyl, 3-cyclopentylpropanoyl, 3-phenylpropanoyl, or 3-methoxycarbonylpropanoyl group.

9. A compound according to claim 1, wherein $R^{17}$ denotes $COR^{12}$, wherein $R^{12}$ denotes a branched or unbranched, saturated $C_{1-7}$-alkyl group substituted with a phenyl, thienyl, cyclopentyl or methoxycarbonyl group.

10. A compound according to claim 1, wherein $R^{17}$ denotes a cinnamoyl group.

11. A compound according to claim 1, wherein said compound is present in the form of a mixture of diastereomers.

12. A compound according to claim 1, wherein said compound is present in the form of an isolated diastereomer substantially free of the opposite diastereomer.

13. A compound according to claim 12, wherein the isolated diastereomer is less polar than the opposite diastereomer.

14. A compound according to claim 1, wherein said compound is a citrate, hydrochloride or methane sulfonate salt.

15. A compound according to claim 1, wherein said compound is a citrate salt.

16. A compound according to claim 15, wherein said citrate salt is a hemicitrate.

17. A compound according to claim 1, selected from the group consisting of:
9 1,1-(3-dimethylamino-3-phenylpentamethylene)-2-(2,3,4,5,6-pentafluorobenzoyl)-1,3,4,9-tetrahydro-2,9-diazafluorene;
50 1,1-(3-dimethylamino-3-(3-fluorophenyl)pentamethylene)-2-cinnamoyl-1,3,4,9-tetrahydro-2,9-diazafluorene;
52 1,1-(3-dimethylamino-3-(3-fluorophenyl)pentamethylene)-2-(cyclopentylcarbonyl)-1,3,4,9-tetrahydro-2,9-diazafluorene;
55 1,1-(3-dimethylamino-3-(3-fluorophenyl)pentamethylene)-2-(2-furylcarbonyl)-1,3,4,9-tetrahydro-2,9-diazafluorene;
56 1,1-(3-dimethylamino-3-phenylpentamethylene)-2-(2-furylcarbonyl)-1,3,4,9-tetrahydro-2,9-diazafluorene;
57 1,1-(3-dimethylamino-3-(3-fluorophenyl)pentamethylene)-2-(4-fluorobenzoyl)-1,3,4,9-tetrahydro-2,9-diazafluorene;
58 1,1-(3-dimethylamino-3-(3-fluorophenyl)pentamethylene)-2-(2-methoxybenzoyl)-1,3,4,9-tetrahydro-2,9-diazafluorene;
60 1,1-(3-dimethylamino-3-(3-fluorophenyl)pentamethylene)-2-(cyclohexylcarbonyl)-1,3,4,9-tetrahydro-2,9-diazafluorene;
61 1,1-(3-dimethylamino-3-(3-fluorophenyl)pentamethylene)-2-benzoyl-1,3,4,9-tetrahydro-2,9-diazafluorene;
62 1,1-(3-dimethylamino-3-phenylpentamethylene)-2-(cyclohexylcarbonyl)-1,3,4,9-tetrahydro-2,9-diazafluorene;
63 1,1-(3-dimethylamino-3-(3-fluorophenyl)pentamethylene)-2-(phenylacetyl)-1,3,4,9-tetrahydro-2,9-diazafluorene;
64 1,1-(3-dimethylamino-3-(3-fluorophenyl)pentamethylene)-2-(4-methoxybenzoyl)-1,3,4,9-tetrahydro-2,9-diazafluorene;
65 1,1-(3-dimethylamino-3-phenylpentamethylene)-2-(4-trifluoromethylbenzoyl)-1,3,4,9-tetrahydro-2,9-diazafluorene;
66 1,1-(3-dimethylamino-3-(3-fluorophenyl)pentamethylene)-2-(thien-2-ylacetyl)-1,3,4,9-tetrahydro-2,9-diazafluorene;
67 1,1-(3-dimethylamino-3-(3-fluorophenyl)pentamethylene)-2-(phenylacetyl)-1,3,4,9-tetrahydro-2,9-diazafluorene;
71 1,1-(3-dimethylamino-3-(3-fluorophenyl)pentamethylene)-2-(2,3-difluorobenzoyl)-1,3,4,9-tetrahydro-2,9-diazafluorene;
72 1,1-(3-dimethylamino-3-(3-fluorophenyl)pentamethylene)-2-(4-methylbenzoyl)-1,3,4,9-tetrahydro-2,9-diazafluorene;
73 1,1-(3-dimethylamino-3-phenylpentamethylene)-2-(3-phenylpropanoyl)-1,3,4,9-tetrahydro-2,9-diazafluorene;
74 1,1-(3-dimethylamino-3-phenylpentamethylene)-2-(3,4-dichlorobenzoyl)-1,3,4,9-tetrahydro-2,9-diazafluorene;
77 1,1-(3-dimethylamino-3-phenylpentamethylene)-2-(3-methoxycarbonylpropanoyl)-1,3,4,9-tetrahydro-2,9-diazafluorene;
78 1,1-(3-dimethylamino-3-(3-fluorophenyl)pentamethylene)-2-(3-chlorobenzoyl)-1,3,4,9-tetrahydro-2,9-diazafluorene;
79 1,1-(3-dimethylamino-3-phenylpentamethylene)-2-(3-fluorobenzoyl)-1,3,4,9-tetrahydro-2,9-diazafluorene;
80 1,1-(3-dimethylamino-3-phenylpentamethylene)-2-(2,6-difluorobenzoyl)-1,3,4,9-tetrahydro-2,9-diazafluorene;
81 1,1-(3-dimethylamino-3-(3-fluorophenyl)pentamethylene)-2-(3,4-dichlorobenzoyl)-1,3,4,9-tetrahydro-2,9-diazafluorene;
84 1,1-(3-dimethylamino-3-phenylpentamethylene)-2-(3-cyclopentylpropanoyl)-1,3,4,9-tetrahydro-2,9-diazafluorene;
85 1,1-(3-dimethylamino-3-(3-fluorophenyl)pentamethylene)-2-(4-fluoro-3-trifluoromethylbenzoyl)-1,3,4,9-tetrahydro-2,9-diazafluorene;
86 1,1-(3-dimethylamino-3-(3-fluorophenyl)pentamethylene)-2-(4-methylbenzoyl)-1,3,4,9-tetrahydro-2,9-diazafluorene;
87 1,1-(3-dimethylamino-3-(3-fluorophenyl)pentamethylene)-2-(3,4,5-trimethoxybenzoyl)-1,3,4,9-tetrahydro-2,9-diazafluorene;
90 1,1-(3-dimethylamino-3-(3-fluorophenyl)pentamethylene)-2-(3-methoxybenzoyl)-1,3,4,9-tetrahydro-2,9-diazafluorene;
91 1,1-(3-dimethylamino-3-phenylpentamethylene)-2-(2-thienylcarbonyl)-1,3,4,9-tetrahydro-2,9-diazafluorene;
93 1,1-(3-dimethylamino-3-(3-fluorophenyl)pentamethylene)-2-(2,4-difluorobenzoyl)-1,3,4,9-tetrahydro-2,9-diazafluorene;
94 1,1-(3-dimethylamino-3-(3-fluorophenyl)pentamethylene)-2-(3,5-difluorobenzoyl)-1,3,4,9-tetrahydro-2,9-diazafluorene;
95 1,1-(3-dimethylamino-3-(3-fluorophenyl)pentamethylene)-2-(4-tert.butylbenzoyl)-1,3,4,9-tetrahydro-2,9-diazafluorene;
97 1,1-(3-dimethylamino-3-(3-fluorophenyl)pentamethylene)-2-(3,4-difluorobenzoyl)-1,3,4,9-tetrahydro-2,9-diazafluorene;
99 1,1-(3-dimethylamino-3-(3-fluorophenyl)pentamethylene)-2-(2-methylbenzoyl)-1,3,4,9-tetrahydro-2,9-diazafluorene;
100 1,1-(3-dimethylamino-3-phenylpentamethylene)-2-(3-phenylpropanoyl)-1,3,4,9-tetrahydro-2,9-diazafluorene;
101 1,1-(3-dimethylamino-3-(3-fluorophenyl)pentamethylene)-2-(3-fluoro-5-trifluoromethylbenzoyl)-1,3,4,9-tetrahydro-2,9-diazafluorene;

102 1,1-(3-dimethylamino-3-phenylpentamethylene)-2-(4-fluoro-3-trifluoro-methylbenzoyl)-1,3,4,9-tetrahydro-2,9-diazafluorene;
103 1,1-(3-dimethylamino-3-(3-fluorophenyl)pentamethylene)-2-(4-nitrobenzoyl)-1,3,4,9-tetrahydro-2,9-diazafluorene;
104 1,1-(3-dimethylamino-3-phenylpentamethylene)-2-(3,5-difluorobenzoyl)-1,3,4,9-tetrahydro-2,9-diazafluorene;
106 1,1-(3-dimethylamino-3-(3-fluorophenyl)pentamethylene)-2-(3,4-difluorobenzoyl)-1,3,4,9-tetrahydro-2,9-diazafluorene;
107 1,1-(3-dimethylamino-3-phenylpentamethylene)-2-(4-chlorobenzoyl)-1,3,4,9-tetrahydro-2,9-diazafluorene;
108 1,1-(3-dimethylamino-3-(3-fluorophenyl)pentamethylene)-2-(3-methylbenzoyl)-1,3,4,9-tetrahydro-2,9-diazafluorene;
109 1,1-(3-dimethylamino-3-(3-fluorophenyl)pentamethylene)-2-(2,3,4,5-tetrafluorobenzoyl)-1,3,4,9-tetrahydro-2,9-diazafluorene;
110 1,1-(3-dimethylamino-3-(3-fluorophenyl)pentamethylene)-2-(2,6-difluorobenzoyl)-1,3,4,9-tetrahydro-2,9-diazafluorene;
111 1,1-(3-dimethylamino-3-phenylpentamethylene)-2-(2-furylcarbonyl)-1,3,4,9-tetrahydro-2,9-diazafluorene;
112 1,1-(3-dimethylamino-3-(3-fluorophenyl)pentamethylene)-2-(2,4-dichlorobenzoyl)-1,3,4,9-tetrahydro-2,9-diazafluorene;
113 1,1-(3-dimethylamino-3-(3-fluorophenyl)pentamethylene)-2-(3-methoxycarbonylpropanoyl)-1,3,4,9-tetrahydro-2,9-diazafluorene;
114 1,1-(3-dimethylamino-3-(3-fluorophenyl)pentamethylene)-2-(3-chlorobenzoyl)-1,3,4,9-tetrahydro-2,9-diazafluorene;
115 1,1-(3-dimethylamino-3-(3-fluorophenyl)pentamethylene)-2-(2-fluoro-5-trifluoromethylbenzoyl)-1,3,4,9-tetrahydro-2,9-diazafluorene;
116 1,1-(3-dimethylamino-3-(3-fluorophenyl)pentamethylene)-2-(2-fluoro-4-trifluoromethylbenzoyl)-1,3,4,9-tetrahydro-2,9-diazafluorene;
119 1,1-(3-dimethylamino-3-phenylpentamethylene)-2-(3,4-difluorobenzoyl)-1,3,4,9-tetrahydro-2,9-diazafluorene;
121 1,1-(3-dimethylamino-3-phenylpentamethylene)-2-(3-methoxycarbonylpropanoyl)-1,3,4,9-tetrahydro-2,9-diazafluorene;
122 1,1-(3-dimethylamino-3-(3-fluorophenyl)pentamethylene)-2-(2-fluoro-6-trifluoromethylbenzoyl)-1,3,4,9-tetrahydro-2,9-diazafluorene;
123 1,1-(3-dimethylamino-3-phenylpentamethylene)-2-(2-methylbenzoyl)-1,3,4,9-tetrahydro-2,9-diazafluorene;
124 1,1-(3-dimethylamino-3-phenylpentamethylene)-2-(3,5-dichlorobenzoyl)-1,3,4,9-tetrahydro-2,9-diazafluorene;
128 1,1-(3-dimethylamino-3-(3-fluorophenyl)pentamethylene)-2-(3-methoxybenzoyl)-1,3,4,9-tetrahydro-2,9-diazafluorene;
131 1,1-(3-dimethylamino-3-(3-fluorophenyl)pentamethylene)-2-(3,5-dichlorobenzoyl)-1,3,4,9-tetrahydro-2,9-diazafluorene;
134 1,1-(3-dimethylamino-3-phenylpentamethylene)-2-(3-nitrobenzoyl)-1,3,4,9-tetrahydro-2,9-diazafluorene;
136 1,1-(3-dimethylamino-3-phenylpentamethylene)-2-(2-thienylacetyl)-1,3,4,9-tetrahydro-2,9-diazafluorene;
137 1,1-(3-dimethylamino-3-phenylpentamethylene)-2-(2-fluoro-4-trifluoromethylbenzoyl)-1,3,4,9-tetrahydro-2,9-diazafluorene;
138 1,1-(3-dimethylamino-3-phenylpentamethylene)-2-(2-fluorobenzoyl)-1,3,4,9-tetrahydro-2,9-diazafluorene;
139 1,1-(3-dimethylamino-3-phenylpentamethylene)-2-(cyclobutylcarbonyl)-1,3,4,9-tetrahydro-2,9-diazafluorene;
140 1,1-(3-dimethylamino-3-phenylpentamethylene)-2-(2-methoxybenzoyl)-1,3,4,9-tetrahydro-2,9-diazafluorene;
141 1,1-(3-dimethylamino-3-phenylpentamethylene)-2-(2,5-difluorobenzoyl)-1,3,4,9-tetrahydro-2,9-diazafluorene;
142 1,1-(3-dimethylamino-3-(3-fluorophenyl)pentamethylene)-2-(2-bromobenzoyl)-1,3,4,9-tetrahydro-2,9-diazafluorene;
143 1,1-(3-dimethylamino-3-phenylpentamethylene)-2-(3-fluoro-5-trifluoromethylbenzoyl)-1,3,4,9-tetrahydro-2,9-diazafluorene;
144 1,1-(3-dimethylamino-3-phenylpentamethylene)-2-(2-fluoro-5-trifluoromethylbenzoyl)-1,3,4,9-tetrahydro-2,9-diazafluorene;
145 1,1-(3-dimethylamino-3-phenylpentamethylene)-2-(2,3-difluorobenzoyl)-1,3,4,9-tetrahydro-2,9-diazafluorene, and
physiologically acceptable salts thereof.

18. 1,1-(3-dimethylamino-3-(3-fluorophenyl)pentamethylene)-2-cinnamoyl-1,3,4,9-tetrahydro-2,9-diazafluorene or a physiologically acceptable salt thereof.

19. A pharmaceutical composition comprising a compound according to claim 1 and at least one pharmaceutically acceptable additive or auxiliary substance.

* * * * *